(12) United States Patent
Liu et al.

(10) Patent No.: US 9,955,676 B2
(45) Date of Patent: May 1, 2018

(54) TRANSGENIC MODEL FOR DELAY-TYPE HYPERSENSITIVITY (DTH) AND USE THEREOF

(71) Applicant: Macau University of Science and Technology, Macau (MO)

(72) Inventors: Liang Liu, Macao (MO); Ting Li, Macao (MO); Kam Wai Wong, Macao (MO); Zhihong Jiang, Macao (MO); Hua Zhou, Macao (MO)

(73) Assignee: Macau University of Science and Technology, Macau (MO)

(*) Notice: Subject to any disclaimer, the term of this patent is extended or adjusted under 35 U.S.C. 154(b) by 0 days. days.

(21) Appl. No.: 14/620,141

(22) Filed: Feb. 11, 2015

(65) Prior Publication Data
US 2016/0037757 A1 Feb. 11, 2016

Related U.S. Application Data

(63) Continuation-in-part of application No. 14/455,951, filed on Aug. 11, 2014, now abandoned.

(60) Provisional application No. 62/038,375, filed on Aug. 18, 2014.

(51) Int. Cl.
*A01K 67/027* (2006.01)
*C12N 15/00* (2006.01)
*A61K 49/00* (2006.01)
*G01N 33/573* (2006.01)
*A61K 31/70* (2006.01)
*G01N 33/574* (2006.01)

(52) U.S. Cl.
CPC ...... *A01K 67/0278* (2013.01); *A61K 49/0008* (2013.01); *G01N 33/573* (2013.01); *A01K 2207/12* (2013.01); *A01K 2227/105* (2013.01); *A01K 2267/01* (2013.01); *A01K 2267/0368* (2013.01); *G01N 33/574* (2013.01); *G01N 2333/91215* (2013.01); *G01N 2800/102* (2013.01); *G01N 2800/44* (2013.01)

(58) Field of Classification Search
CPC ........ A01K 67/0278; A01K 2267/0368; A01K 2267/01; A01K 2227/105; A61K 49/008
See application file for complete search history.

(56) References Cited

U.S. PATENT DOCUMENTS

| | | | | |
|---|---|---|---|---|
| 5,614,396 A | * | 3/1997 | Bradley et al. | 435/463 |
| 6,753,456 B2 | * | 6/2004 | Lester | A01K 67/0275 800/18 |
| 2003/0024001 A1 | * | 1/2003 | Kwak | A01K 67/0275 800/18 |
| 2005/0144659 A1 | * | 6/2005 | Baron | A01K 67/0275 800/18 |
| 2013/0210875 A1 | * | 8/2013 | Liu | A61K 31/352 514/387 |

OTHER PUBLICATIONS

Li et al. A novel drug binding site of cysteine-46 on IKK-beta kinase is responsible for suppressionof IKK-beta-NF-kappaB signaling and inflammation. Chin. J. Pharmacol. Toxicol. 26:721, Oct. 2012.*
Kapahi et al. Inhibition of NF-kappaB activation by arsenite through reaction with a critical cysteine in the activation loop of IkappaB kinase. J. Biol. Chem. 275:36062-36066, 2000.*
Li et al. IKKbeta is required for peripheral B cell survival and proliferation. J. Immunol. 170:4630-4637, 2003.*
GenBank Accession No. AF026524.1. Mus musculus IKB kinase beta (IKKbeta) mRNA, complete cds, 1998, 2 pages.*
Mullins et al. Perspectives Series: Molecular Medicine in genetically engineered animals. J. Clin. Invest. 98:Supplement S37-S40, 1996.*
Wall R.J. Transgenic livestocks: Progress and prospects for the future. Theriogenology 45:57-68, 1996.*
Li et al. Mutation of cysteine 46 in IKK-beta increases inflammatory responses. Oncotarget 6(31):31805-31819. doi:10.18632/oncotarget.5567, 2015.*

* cited by examiner

*Primary Examiner* — Quang Nguyen
(74) *Attorney, Agent, or Firm* — Spruson & Ferguson (Hong Kong) Limited

(57) ABSTRACT

The present invention provides an in vivo platform for identifying and determining therapeutic or prophylactic activity of test compounds in delay-type hypersensitivity (DTH) and other inflammatory or cancerous diseases mediated by activation of IKK-$\beta^{C46A}$ mutants. The in vivo platform of the present invention is a non-human transgenic mammal, e.g., a mouse model, with a site directed mutagenesis at a cysteine residue replaced by alanine in IKK-$\beta$ protein kinase. The site directed mutagenesis is introduced by a specially designed targeting vector containing a transversion in exon 3 of the Ikbkb genes encoding the IKK-$\beta$. The present invention also provides methods for generating the transgenic mammal and for determining and identifying compounds that can inhibit activation of IKK-$\beta^{C46A}$ mutants.

10 Claims, 16 Drawing Sheets

SEQUENCE LISTING

```
<160> NUMBER OF SEQ ID NOS: 16

<210> SEQ ID NO 1
<211> LENGTH: 14183
<212> TYPE: DNA
<213> ORGANISM: Mus musculus

<400> SEQUENCE: 1
gacaagggaa aactcaccgc agacctgtga tatgcagact tgtgaactaa aagatgtatt      60
catgttgttt taagcaactg ggcctgtggc taattcatta caattgaaca agaaaacaac     120
tcactgctct gtgtgttaaa gttagatgtg tgcagactct ttagtctccg agcatggact     180
ctttcatcct cgggtagcat agcagaactg taacatcttc atgtaaccac agaaccacca     240
gcatactagc tataggagtg tctggaccag agatcttctg cagcgagctt gccctgccc     300 ggacccgctt ccacgcctct gcagaaccct gttttccaca agtctaggct ctgactaaag     360
gccagtgtag agttcttgag tcttggtaat ctatttttaa tggtaataat aacctttact     420
caagtgaata aaactcacct tccaaccatt tgagaaataa tttaatatag atttttctta     480
ggtggccgtg tttctcttaa atatattatt aatgtgttct ttgacaattt tgtacatgta     540
cataatattt ttggatcatg ttcatcccat taccctctct tatccctctt cactaaaacc     600
cttcttgttc tcacatcccc ctaccttcgt atcttgcagg tatgtgtgac ccattgggct     660
taattaaggt tgcctatatg agcctgggcg gggtgttagg ctgattgact tgtaaggcag     720
agatcaaggc tctggtcatt tcagacaggc actttctctc acttaaagac atgtcttcca     780
ctgtgccgtc acaaaggtct ctacatgata gcatctcacc gtggctgcct gcaacccccat    840 cagcttctcc gcagccccac ctctcaatgc tgttacaaaa gtaattacgt ttcaacactc     900
taacctcagc attcaacatc agtggggttt gctgttgacg aatccaccct agaactgggc     960
aagaaaatat ttgagtccca gcactgacag gaagtgaaac tgaggacggt tccagtcggc    1020
ttgagaggag ggagactcgt tggaagctca agatctcgaa gcacggtgtt ttccaggctg    1080
tggcttctga gaatgtccgt ccattagagg aatgttttc tagtatggtc gctcactctt     1140
gaagaccaga gatggacttc tccctgggtt ctgctgtgtt cagcagccat agtggatata    1200
gtgtggaaag gaaatcagct cttcagagag agcctcagaa tccaggccaa aaccaggatt    1260 ctttttttt tttttcatt tttattaggt atttagctca tttacatttc caatgctata     1320
ccaaaagtcc cccatatccca cccaccccca ctcccctacc cacccactcc ccaaaaccag    1380
gattctaaca gacaaagaaa aggagagaat gatggtgggg cagaccccag ttaatgatac    1440
ctcctcccgt gggcggccat gaggaggctg ttgaggtcac aagagtggac ccgtagccgc    1500
agtgtgagtg aactgtggct ttaagcgaga gcgtctgtgt aaaatttcac acatgtgact    1560
tgttttacac ggaatgtcca gagcatgtaa atccacacag acagaaagta gatgtgtgtt    1620
gtctaggggt tgtaaagacg ccagggacga tgggaagtgg gtggggtttg tgggtggaga    1680
```

```
ccctgctcca gcatcagctg tgattttggt tgtatactta aatagacca gaaaactagg    1740 catggacgta agtgcatctt agacagctta agcagtagtt ctcgattaaa aacacatcct    1800
gagaacattt tagaggtttt gttatatttg tgctccggca ttagaatggt gatgaccacc    1860
ctcatttctg aagttgtcag tcttaatcat ccatttcagg gtggatttct taatcattga    1920
tcacattaga taactcctcc tggtgtttgg agcgttctct taccagcgtt tcccaagcag    1980
cagcaggagt tttgggtgac cgtgaggcag tgatcctgtc ggatgctgat gacagccgcc    2040
tgcttgtctt gccagggtcc tgtgcgtgtt ggtttaactc attactgtac gaatcacaca    2100
ctttaaagtt ttaggattct ttttatagaa tgtacaagtg cggaaatggt ctatggggcc    2160
tctaggactt ctttcatggg gccaacagta ttatctgtgc tgattaaagt tgattttaaa    2220
ggtctttaga ggttttagtc ttttgccttt tacctataga agcagaaatc ttgttttgta    2280
tggaaaataa cccaccatca gttttgaata tgtgaagtgt ttttttgtttt tgtttttaag    2340 tttgtagcaa gcagaaatga aaaataaat agccaacagc taaatagcca acagtagaca    2400
ggtaaacagc agagcagctt caagataggc gcctacacca tccagagaga gcgatcagga    2460
gtagtccaac tggcagcgaa tactgaagct tcctcagata ggtgcttacg ccatccatca    2520
gaaatcccct ggggaagccc ttgctgagtt cccagatgag agctctccag acagaataga    2580
gcatgctctc catggatgaa cttctgcctt cctgttcttg ctacaggtat ttttttatacc    2640 gtgcaaaaca ccgcagtaag ctctgttggg aggcttatc cctagctgtt ctcagtggcg    2700
tcaccgtgaa cagggacgct gatactactg tccaaagtcg aggctgccct ggtggttcca    2760
ggacacctga caccagggct tctctctgct gccactgccc aacccacagc tcagaaccct    2820
cctctcctac gtgttcccat ggtctccttt ttgtaccagc aaagagatgc ctgttaacct    2880
caggagccag tcataagtca caaaatactg actctttcag taaaaaaccc acacagtgtg    2940
gttaagggtg taatttggtt ggtagagtgc ttatccagtg ttcacaaagc cctaggtttg    3000
atccccagcg ccatataaag tgggcgtggt ggtccatgca cacctgtaat cttagcatat    3060
ggtaagatgc gtcaggagga tcagaaatcc agtgtcatcc ttgtagccat agtgaatatc    3120
agtctaggct tggatccatt agaccattct acagtaaata aggatgtaaa taaataatga    3180
aagcaggctt tggaagagta tatgccatac tctcaggact gtgctcttgt gaattgtcag    3240
gcacttgcta tgggctttct atctgtatga tatagctaca tctctgtcct cattacagcc    3300
ctgagctgtg gcaggtcagt attcctgttg cataagtgaa gacacagtct gtatgtagtt    3360
tgctccaagg atacacagct ggtgaaagag agttggaacc tgagctgttc tgtgtctcat    3420
tgactacact atgtttgtct tctctccaaa gagaaaggaa aaaacaaaaa acctcttaca    3480
tgaaacaagg gagacactca ctgggccagt agttgaatca atcacacgga agcgccactt    3540
ttatatgtga aacaggccaa tcaccagcag cgctggatgg cttaacctgg cattattacc    3600
acggcaacag ttagcgtgtg cagagagaag tagaagcccc ggacagggt gtgctacagg    3660 ggggcagggg tgtggaggag gcagcgacag agcaagatgt gaagaatttg tgcccctcg    3720 atggatagat gcagcgggaa gatgggcaaa ctgtgatgtg gggtggtga ggagggcaga    3780 cagacagaca gacaggcagg ccagccaggt ggagagtaag gtatggatgc ccgtgaattc    3840
cgaagttcct attctctaga aagtatagga acttcaggtc tgaagaggag tttacgtcca    3900
gccaagctag cttggctgca ggtcgtcgaa attctaccgg gtaggggagg cgcttttccc    3960
aaggcagtct ggagcatgcg ctttagcagc cccgctgggc acttggcgct acacaagtgg    4020
cctctggcct cgcacacatt ccacatccac cggtaggcgc caaccggctc cgttctttgg    4080
```

```
tggcccette gegccacett ctactcctcc cctagtcagg aagttccccc ccgccccgca    4140
gctcgcgtcg tgcaggacgt gacaaatgga agtagcacgt ctcactagtc tcgtgcagat    4200
ggacagcacc gctgagcaat ggaagcgggt aggcctttgg ggcagcggcc aatagcagct    4260
ttgctccttc gctttctggg ctcagaggct gggaaggggt gggtccgggg gcgggctcag    4320 ggcgggctc aggggcgggg cgggcgcccg aaggtcctcc ggaggcccgg cattctgcac     4380
gcttcaaaag cgcacgtctg ccgcgctgtt ctcctcttcc tcatctccgg gcctttcgac    4440
ctgcagcctg ttgacaatta atcatcggca tagtatatcg gcatagtata atacgacaag    4500
gtgaggaact aaaccatggg atcggccatt gaacaagatg gattgcacgc aggttctccg    4560
gccgcttggg tggagaggct attcggctat gactgggcac aacagacaat cggctgctct    4620
gatgccgccg tgttccggct gtcagcgcag gggcgcccgg ttcttttgt caagaccgac     4680 ctgtccggtg ccctgaatga actgcaggac gaggcagcgc ggctatcgtg gctggccacg    4740
acgggcgttc cttgcgcagc tgtgctcgac gttgtcactg aagcgggaag gactggctg     4800 ctattgggcg aagtgccggg gcaggatctc ctgtcatctc accttgctcc tgccgagaaa    4860
gtatccatca tggctgatgc aatgcggcgg ctgcatacgc ttgatccggc tacctgccca    4920
ttcgaccacc aagcgaaaca tcgcatcgag cgagcacgta ctcggatgga agccggtctt    4980
gtcgatcagg atgatctgga cgaagagcat caggggctcg cgccagccga actgttcgcc    5040
aggctcaagg cgcgcatgcc cgacggcgat gatctcgtcg tgacccatgg cgatgcctgc    5100
ttgccgaata tcatggtgga aaatggccgc ttttctggat tcatcgactg tggccggctg    5160
ggtgtggcgg accgctatca ggacatagcg ttggctaccc gtgatattgc tgaagagctt    5220
ggcggcgaat gggctgaccg cttcctcgtg ctttacggta tcgccgctcc cgattcgcag    5280
cgcatcgcct tctatcgcct tcttgacgag ttcttctgag gggatcaatt ctctagagct    5340
cgctgatcag cctcgactgt gccttctagt tgccagccat ctgttgtttg cccctcccc    5400 gtgccttcct tgaccctgga aggtgccact cccactgtcc tttcctaata aaatgaggaa    5460
attgcatcgc attgtctgag taggtgtcat tctattctgg ggggtggggt ggggcaggac    5520
agcaaggggg aggattggga agacaatagc aggcatgctg gggatgcggt gggctctatg    5580
gcttctgagg cggaaagaac cagctggggc tcgactagag cttgcggaac ccttcgaagt    5640
tcctattctc tagaaagtat aggaacttca tcagtcaggt acataatata acttcgtata    5700
atgtatgcta tacgaagtta ttaggtggat ccactagttc tagagcggcc gccaccgcgg    5760
tccaggtgtt ctgcaggatg cctgtatggc actggggttc tgcggtggtc ataggtctgg    5820
ttgtccatcg ctctgacgtc cagcgtgccc tctctgtagg cgacaggtga acagatcgcc    5880
atcaagcaag cccgacagga gctcagccca agaacagaag accgctggtg cctcgaaatc    5940
cagatcatga gaaggtgagg ggcctgggcc cacagcgggg gcggggagg ggtcatttcc     6000 acagccctgt gacccgggaa tgaatagcat agaaaagagc cccgcagtgt cttctgtcag    6060
cacagtgccc acattattta gataggtcgc tgtcctggag gcttctagag gagtaacatt    6120
taagcactac attgagctat gtggtcagtt tgttgcgtta aacgtaagac agccatctta    6180
cctaggcgtg gtgttgtgct tctataggac aaggaagaag gctgggagg ttgaagacag     6240 gaggaatagt tgagcccagg aatttgagac cagcatagac aacctaacac actgtatcag    6300
acattgctta attaataagt taattaaagc agttagcaag ttttgatttg tcagcagaaa    6360
tctttgtttt ccctatgttt ctaattgcac agtggcatgc gactcgctgt ttgccctctg    6420
```

```
gggagagtca cacagtgcgg acacaggatc tttcaggcct gcctgggtgg atgctgtccc    6480
ccccagctag tgggacctgt agtggcgagc actccgagaa ttagctcgaa gaaatcaagc    6540
agaagccccc cacagctcac gtccttcatt tttaaaatca ctctattttg tgtgtgtggg    6600
tggcttggct gcatctgtgt ctgtgcatca catgcatgct tggtgcctgg gctggccagg    6660
aggggcactt gggtctgctg gaactggagt ttagagaact cagccacatc ggggcttgga    6720
cttaaaccca ggtcctctgg aagagccctg tcgaatcatc tctccagacc tctgctcacg    6780
tcttaaaaga tgggaaagag cagtgtctcc tttgttgaat gtccacatgc atgcctgtgc    6840
cagccttttc ccttaagtgg cataaggtta cctgttgtca cctatcagaa gcagtcttac    6900
agacactgaa aaatggagat aggacccttt aaggacaatt aaatgatctg cgatgtactt    6960
gtcgggtgtt tgagttcaga ggctgagcaa ggccgggtaa atatttaact tggtagagtc    7020
ccaggtgagt ctctcatccc tgaaccccca tcttctcctg tgtagtcacc aagaatgcct    7080
ggttattctt tgccttcgtt agaaggtgag atggtgtgag acatggaata agagggatgg    7140
atttgagctg aaccccggag gcttattctt tcccctcttt ctaggctgaa ccatcccaat    7200
gtggtggctg cccgggatgt cccagagggg atgcagaacc tggcacccaa tgatttgcca    7260
ctgctggcca tggagtactg ccaaggagga gatctccgaa gagtgagtct tctgggggttg   7320 tgggattgtg ggatgttggt ccatttgggc cactctggaa cactgggagg ggagacaagg    7380
agagatctct agccatcatc caggaagctc aaagagtcag ggaagtatct tcacctgctc    7440
agcctccctc tttctatgcct tctttgggggt ggtttctgtg cgtgcaaatc aaaaggctga   7500
gtcaggagtg cccacaagaa ggctgaatac gggccgggtc acatggtcgc taacatgaca    7560
aggaaaagtt accatcaggc ctggaccacg ggaagaaact gaatgagtct cagaacacac    7620
tcttcccctc tggcacatta gagccactgc aagcttttgg ggttggcgtc accactgtcc    7680
aatggggtga gacttttttc atagacatta cagtgccaca cagaatcaca gcgggcagga    7740
agggagccag cttagtcatc agagaacagg gttgcagttc caggccctcc tgactcacct    7800
cagggcttcc cctttccctc tcctgtcctg tatctgctct catcgcacac tggacagtgg    7860
gcgtcggcta ttctcccttg tcacacggac agttctgtat gccacccaga tagagaatcc    7920
ttatgctttt acagggtgcc tggtttatgg ttccaatata ttggcaccca gatagagttc    7980
ctgcactgta ggtggatatc atggcccaga gacactaatt aggcaaagcc ctggctacat    8040
acagctgtgg actagagaga gcctggaccg taggccatct caggtgcagg cggcttgctg    8100
tctgtgaaca cgggtcatgt ccgttttgag aaaaataaac tctccaagtg agatttttt     8160 tttatttaat ctattcttcc aatagctcca ttcagctctt tattctaaac gagcctcagc    8220
acgtggcttg gccgcccctt cacctctctc tctacactgc agtttcccag actcacgtca    8280
tgtgctgtgc tcttcatcct tccgggcctt tcgtcactag tggatcctct agagtcgagc    8340
agtgtggttt tcaagaggaa gcaaaaagcc tctccaccca ggcctggaat gtttccaccc    8400
aatgtcgagc agtgtggttt tgcaagagga agcaaaaagc ctctccaccc aggcctggaa    8460
tgtttccacc caatgtcgag caaaccccgc ccagcgtctt gtcattggcg aattcgaaca    8520
cgcagatgca gtcggggcgg cgcggtccca ggtccacttc gcatattaag gtgacgcgtg    8580
tggcctcgaa caccgagcga ccctgcagcg acccgcttaa cagcgtcaac agcgtgccgc    8640
agatcttggt ggcgtgaaac tcccgcacct cttcggccag cgccttgtag aagcgcgtat    8700
ggcttcgtac cccggccatc agcacgcgtc tgcgttcgac caggctgcgc gttctcgcgg    8760
ccatagcaac cgacgtacgg cgttgcgccc tcgccggcag caagaagcca cggaagtccg    8820
```

```
cccggagcag aaaatgccca cgctactgcg ggtttatata gacggtcccc acgggatggg    8880
gaaaaccacc accacgcaac tgctggtggc cctgggttcg cgcgacgata tcgtctacgt    8940
acccgagccg atgacttact ggcgggtgct gggggcttcc gagacaatcg cgaacatcta    9000
caccacacaa caccgccttg accagggtga gatatcggcc ggggacgcgg cggtggtaat    9060
gacaagcgcc cagataacaa tgggcatgcc ttatgccgtg accgacgccg ttctggctcc    9120
tcatatcggg ggggaggctg ggagctcaca tgccccgccc ccggccctca ccctcatctt    9180
cgaccgccat cccatcgccg ccctcctgtg ctacccggcc gcgcgatacc ttatgggcag    9240
catgaccccc caggccgtgc tggcgttcgt ggccctcatc ccgccgacct tgcccggcac    9300
aaacatcgtg ttgggggccc ttccggagga cagacacatc gaccgcctgg ccaaacgcca    9360
gcgcccggc gagcggcttg acctggctat gctggccgcg attcgccgcg tttacgggct    9420
gcttgccaat acggtgcggt atctgcaggg cggcgggtcg tggcgggagg attggggaca    9480
gctttcgggg acggccgtgc cgccccaggg tgccgagccc cagagcaacg cgggcccacg    9540
accccatatc ggggacacgt tatttaccct gtttcgggcc cccgagttgc tggccccaa    9600
cggcgacctg tacaacgtgt ttgcctgggc cttggacgtc ttggccaaac gcctccgtcc    9660
catgcacgtc tttatcctgg attacgacca atcgcccgcc ggctgccggg acgccctgct    9720
gcaacttacc tccgggatga tccagaccca cgtcaccacc ccaggctcca taccgacgat    9780
ctgcgacctg gcgcgcacgt ttgcccggga gatggggag gctaactgaa acacggaagg    9840
agacaatacc ggaaggaacc cgcgctatga cggcaataaa aagacagaat aaaacgcacg    9900
ggtgttgggt cgtttgttca taaacgcggg gttcggtccc agggctggca ctctgtcgat    9960
accccaccga gacccattg gggccaatac gcccgcgttt cttcctttc cccacccca   10020
cccccaagtt cgggtgaagg cccagggctc gcagccaacg tcggggcggc aggccctgcc   10080
atagccacgg gcccccgtggg ttagggacgg ggtccccat ggggaatggt ttatggttcg   10140
tgggggttat tattttgggc gttgcgtggg gtcagtccac gactggactg agcagacaga   10200
cccatggttt ttggatggcc tgggcatgga ccgcatgtac tggcgcgaca cgaacaccgg   10260
gcgtctgtgg ctgccaaaca cccccgaccc ccaaaaacca ccgcgcggat ttctggcgcc   10320
gccggacgaa ctaaacctga ctacggcatc tctgccccct cttcgctggt acgaggagcg   10380
cttttgtttt gtattggtca ccacggccga gtttcctcga ccgatgccct tgagagcctt   10440
caacccagtc agctccttcc ggtgggcgcg gggcatgact atcgtcgccg cacttatgac   10500
tgtcttcttt atcatgcaac tcgtaggaca ggtgccggca gcgctctggg tcattttcgg   10560
cgaggaccgc tttcgctgga gcgcgacgat gatcggcctg tcgcttgcgg tattcggaat   10620
cttgcacgcc ctcgctcaag ccttcgtcac tggtcccgcc accaaacgtt tcggcgagaa   10680
gcaggccatt atcgccggca tggcggccga cgcgctgggc tacgtcttgc tggcgttcgc   10740
gacgcgaggc tggatggcct tccccattat gattcttctc gcttccggcg catcgggat   10800
gcccgcgttg caggccatgc tgtccaggca ggtagatgac gaccatcagg gacagcttca   10860
aggatcgctc gcggctctta ccagcctaac ttcgatcact ggaccgctga tcgtcacggc   10920
gatttatgcc gcctcggcga gcacatggaa cgggttggca tggattgtag gcgccgccct   10980
ataccttgtc tgcctccccg cgttgcgtcg cggtgcatgg agccgggcca cctcgacctg   11040
aatggaagcc ggcggcacct cgctaacgga ttcaccactc caagaattgg agccaatcaa   11100
ttcttgcgga gaactgtgaa tgcgcaaacc aacccttggc agaacatatc catcgcgtcc   11160
```

```
gccatctcca gcagccgcac gcggcgcatc tcgggcagcg ttgggtcctg gccacgggtg   11220
cgcatgatcg tgctcctgtc gttgaggacc cggctaggct ggcggggttg ccttactggt   11280
tagcagaatg aatcaccgat acgcgagcga acgtgaagcg actgctgctg caaaacgtct   11340
gcgacctgag caacaacatg aatggtcttc ggtttccgtg tttcgtaaag tctggaaacg   11400
cggaagtcag cgccctgcac cattatgttc cggatctgca tcgcaggatg ctgctggcta   11460
ccctgtggaa cacctacatc tgtattaacg aagcgctggc attgaccctg agtgattttt   11520
ctctggtccc gccgcatcca taccgccagt tgtttaccct cacaacgttc cagtaaccgg   11580
gcatgttcat catcagtaac ccgtatcgtg agcatcctct ctcgtttcat cggtatcatt   11640 accccccatga acagaaatcc cccttacacg gaggcatcag tgaccaaaca ggaaaaaacc   11700
gcccttaaca tggcccgctt tatcagaagc cagacattaa cgcttctgga gaaactcaac   11760
gagctggacg cggatgaaca ggcagacatc tgtgaatcgc ttcacgacca cgctgatgag   11820
ctttaccgca gctgcctcgc gcgtttcggt gatgacggtg aaaacctctg acacatgcag   11880
ctcccggaga cggtcacagc ttgtctgtaa gcggatgccg ggagcagaca agcccgtcag   11940
ggcgcgtcag cgggtgttgg cgggtgtcgg ggcgcagcca tgacccagtc acgtagcgat   12000
agcggagtgt atactggctt aactatgcgg catcagagca gattgtactg agagtgcacc   12060
atatgcggtg tgaaataccg cacagatgcg taaggagaaa ataccgcatc aggcgctctt   12120
ccgcttcctc gctcactgac tcgctgcgct cggtcgttcg gctgcggcga gcggtatcag   12180
ctcactcaaa ggcggtaata cggttatcca cagaatcagg ggataacgca ggaaagaaca   12240
tgtgagcaaa aggccagcaa aaggccagga accgtaaaaa ggccgcgttg ctggcgtttt   12300
tccataggct ccgcccccct gacgagcatc acaaaaatcg acgctcaagt cagaggtggc   12360
gaaacccgac aggactataa agataccagg cgtttccccc tggaagctcc ctcgtgcgct   12420
ctcctgttcc gaccctgccg cttaccggat acctgtccgc ctttctccct tcgggaagcg   12480
tggcgctttc tcatagctca cgctgtaggt atctcagttc ggtgtaggtc gttcgctcca   12540
agctgggctg tgtgcacgaa ccccccgttc agcccgaccg ctgcgcctta tccggtaact   12600
atcgtcttga gtccaacccg gtaagacacg acttatcgcc actggcagca gccactggta   12660
acaggattag cagagcgagg tatgtaggcg gtgctacaga gttcttgaag tggtggccta   12720
actacggcta cactagaagg acagtatttg gtatctgcgc tctgctgaag ccagttacct   12780
tcggaaaaag agttggtagc tcttgatccg gcaaacaaac caccgctggt agcggtggtt   12840 ttttgtttg caagcagcag attacgcgca gaaaaaagg atctcaagaa gatcctttga   12900
tcttttctac ggggtctgac gctcagtgga acgaaaactc acgttaaggg attttggtca   12960
tgagattatc aaaaaggatc ttcacctaga tccttttaaa ttaaaaatga agttttaaat   13020
caatctaaag tatatatgag taaacttggt ctgacagtta ccaatgctta atcagtgagg   13080
cacctatctc agcgatctgt ctatttcgtt catccatagt tgcctgactc cccgtcgtgt   13140
agataactac gatacgggag ggcttaccat ctggccccag tgctgcaatg ataccgcgag   13200
acccacgctc accggctcca gatttatcag caataaacca gccagccgga agggccgagc   13260
gcagaagtgg tcctgcaact ttatccgcct ccatccagtc tattaattgt tgccgggaag   13320
ctagagtaag tagttcgcca gttaatagtt tgcgcaacgt tgttgccatt gctgcaggca   13380
tcgtggtgtc acgctcgtcg tttggtatgg cttcattcag ctccggttcc caacgatcaa   13440
ggcgagttac atgatccccc atgttgtgca aaaaagcggt tagctccttc ggtcctccga   13500
tcgttgtcag aagtaagttg gccgcagtgt tatcactcat ggttatggca gcactgcata   13560
```

-continued

```
attctcttac tgtcatgcca tccgtaagat gcttttctgt gactggtgag tactcaacca    13620
agtcattctg agaatagtgt atgcggcgac cgagttgctc ttgcccggcg tcaacacggg    13680
ataataccgc gccacatagc agaactttaa aagtgctcat cattggaaaa cgttcttcgg    13740
ggcgaaaact ctcaaggatc ttaccgctgt tgagatccag ttcgatgtaa cccactcgtg    13800
cacccaactg atcttcagca tcttttactt tcaccagcgt ttctgggtga gcaaaaacag    13860
gaaggcaaaa tgccgcaaaa aagggaataa gggcgacacg gaaatgttga atactctatc    13920
tcttcctttt tcaatattat tgaagcattt atcagggtta ttgtctcatg agcggataca    13980
tatttgaatg tatttagaaa aataaacaaa taggggttcc gcgcacattt ccccgaaaag    14040
tgccacctga cgtctaagaa accattatta tcatgacatt aacctataaa aataggcgta    14100
tcacgaggcc ctttcgtctt caagaattct catgttttgac agcttatcat cgataagctg    14160
cggccgcaaa ggccgcggtc gac                                             14183
```

<210> SEQ ID NO 2
<211> LENGTH: 735
<212> TYPE: PRT
<213> ORGANISM: Mus musculus

<400> SEQUENCE: 2

```
Met Ser Trp Ser Pro Ser Leu Pro Thr Gln Thr Cys Gly Ala Trp Glu
1               5                   10                  15

Met Lys Glu Arg Leu Gly Thr Gly Gly Phe Gly Asn Val Ile Arg Trp
                20                  25                  30

His Asn Gln Ala Thr Gly Glu Gln Ile Ala Ile Lys Gln Ala Arg Gln
            35                  40                  45

Glu Leu Ser Pro Lys Asn Arg Asp Arg Trp Cys Leu Glu Ile Gln Ile
        50                  55                  60

Met Arg Arg Leu Asn His Pro Asn Val Val Ala Ala Arg Asp Val Pro
65                  70                  75                  80

Glu Gly Met Gln Asn Leu Ala Pro Asn Asp Leu Pro Leu Leu Ala Met
                85                  90                  95

Glu Tyr Cys Gln Gly Gly Asp Leu Arg Arg Tyr Leu Asn Gln Phe Glu
            100                 105                 110

Asn Cys Cys Gly Leu Arg Glu Gly Ala Val Leu Thr Leu Leu Ser Asp
        115                 120                 125

Ile Ala Ser Ala Leu Arg Tyr Leu His Glu Asn Arg Ile Ile His Arg
130                 135                 140

Asp Leu Lys Pro Glu Asn Ile Val Leu Gln Gln Gly Glu Lys Arg Leu
145                 150                 155                 160

Ile His Lys Ile Ile Asp Leu Gly Tyr Ala Lys Glu Leu Asp Gln Gly
                165                 170                 175

Ser Leu Cys Thr Ser Phe Val Gly Thr Leu Gln Tyr Leu Ala Pro Glu
            180                 185                 190

Leu Leu Glu Gln Gln Lys Tyr Thr Val Thr Val Asp Tyr Trp Ser Phe
        195                 200                 205

Gly Thr Leu Ala Phe Glu Cys Ile Thr Gly Phe Arg Pro Phe Leu Pro
210                 215                 220

Asn Trp Gln Pro Val Gln Trp His Ser Lys Val Arg Gln Lys Ser Glu
225                 230                 235                 240

Val Asp Ile Val Val Ser Glu Asp Leu Asn Gly Ala Val Lys Phe Ser
                245                 250                 255
```

```
Ser Ser Leu Pro Phe Pro Asn Asn Leu Asn Ser Val Leu Ala Glu Arg
            260                 265                 270

Leu Glu Lys Trp Leu Gln Leu Met Leu Met Trp His Pro Arg Gln Arg
        275                 280                 285

Gly Thr Asp Pro Gln Tyr Gly Pro Asn Gly Cys Phe Arg Ala Leu Asp
    290                 295                 300

Asp Ile Leu Asn Leu Lys Leu Val His Val Leu Asn Met Val Thr Gly
305                 310                 315                 320

Thr Val His Thr Tyr Pro Val Thr Glu Asp Glu Ser Leu Gln Ser Leu
                325                 330                 335

Lys Thr Arg Ile Gln Glu Asp Thr Gly Ile Leu Glu Thr Asp Gln Glu
            340                 345                 350

Leu Leu Gln Glu Ala Gly Leu Val Leu Leu Pro Asp Lys Pro Ala Thr
        355                 360                 365

Gln Cys Ile Ser Asp Ser Lys Thr Asn Glu Gly Leu Thr Leu Asp Met
    370                 375                 380

Asp Leu Val Phe Leu Phe Asp Asn Ser Lys Ile Asn Tyr Glu Thr Gln
385                 390                 395                 400

Ile Thr Pro Arg Pro Gln Pro Glu Ser Val Ser Cys Ile Leu Gln Glu
                405                 410                 415

Pro Lys Arg Asn Leu Ser Phe Phe Gln Leu Arg Lys Val Trp Gly Gln
            420                 425                 430

Val Trp His Ser Ile Gln Thr Leu Lys Glu Asp Cys Asn Arg Leu Gln
        435                 440                 445

Gln Gly Gln Arg Ala Ala Met Met Ser Leu Leu Arg Asn Asn Ser Cys
    450                 455                 460

Leu Ser Lys Met Lys Asn Ala Met Ala Ser Thr Ala Gln Gln Leu Lys
465                 470                 475                 480

Ala Lys Leu Asp Phe Phe Lys Thr Ser Ile Gln Ile Asp Leu Glu Lys
                485                 490                 495

Tyr Lys Glu Gln Thr Glu Phe Gly Ile Thr Ser Asp Lys Leu Leu Leu
            500                 505                 510

Ala Trp Arg Glu Met Glu Gln Ala Val Glu Gln Cys Gly Arg Glu Asn
        515                 520                 525

Asp Val Lys His Leu Val Glu Arg Met Met Ala Leu Gln Thr Asp Ile
    530                 535                 540

Val Asp Leu Gln Arg Ser Pro Met Gly Arg Lys Gln Gly Gly Thr Leu
545                 550                 555                 560

Asp Asp Leu Glu Glu Gln Ala Arg Glu Leu Tyr Arg Arg Leu Arg Glu
                565                 570                 575

Lys Pro Arg Asp Gln Arg Thr Glu Gly Asp Ser Gln Glu Met Val Arg
            580                 585                 590

Leu Leu Leu Gln Ala Ile Gln Ser Phe Glu Lys Lys Val Arg Val Ile
        595                 600                 605

Tyr Thr Gln Leu Ser Lys Thr Val Cys Lys Gln Lys Ala Leu Glu
    610                 615                 620

Leu Leu Pro Lys Val Glu Glu Val Val Ser Leu Met Asn Glu Asp Glu
625                 630                 635                 640

Arg Thr Val Val Arg Leu Gln Glu Lys Arg Gln Lys Glu Leu Trp Asn
                645                 650                 655

Leu Leu Lys Ile Ala Cys Ser Lys Val Arg Gly Pro Val Ser Gly Ser
            660                 665                 670

Pro Asp Ser Met Asn Val Ser Arg Leu Ser His Pro Gly Gln Leu Met
```

```
                675                 680                 685
Ser Gln Pro Ser Ser Ala Cys Asp Ser Leu Pro Glu Ser Asp Lys Lys
        690                 695                 700

Ser Glu Glu Leu Val Ala Glu Ala His Ala Leu Cys Ser Arg Leu Glu
705                 710                 715                 720

Ser Ala Leu Gln Asp Thr Val Lys Glu Gln Asp Arg Ser Phe Thr
            725                 730                 735

<210> SEQ ID NO 3
<211> LENGTH: 24
<212> TYPE: DNA
<213> ORGANISM: Artificial Sequence
<220> FEATURE:
<223> OTHER INFORMATION: ES-5-up forward primer

<400> SEQUENCE: 3
acgttggtgg gtttgaggat gagg                                           24

<210> SEQ ID NO 4
<211> LENGTH: 21
<212> TYPE: DNA
<213> ORGANISM: Artificial Sequence
<220> FEATURE:
<223> OTHER INFORMATION: ES-5-down reverse primer

<400> SEQUENCE: 4
ctgagcccag aaagcgaagg a                                              21

<210> SEQ ID NO 5
<211> LENGTH: 23
<212> TYPE: DNA
<213> ORGANISM: Artificial Sequence
<220> FEATURE:
<223> OTHER INFORMATION: ES-3-up forward primer

<400> SEQUENCE: 5
gtgccactcc cactgtcctt tcc                                            23

<210> SEQ ID NO 6
<211> LENGTH: 26
<212> TYPE: DNA
<213> ORGANISM: Artificial Sequence
<220> FEATURE:
<223> OTHER INFORMATION: ES-3-down reverse primer

<400> SEQUENCE: 6
actccggcct gaagtccttg cctatg                                         26

<210> SEQ ID NO 7
<211> LENGTH: 31
<212> TYPE: DNA
<213> ORGANISM: Artificial Sequence
<220> FEATURE:
<223> OTHER INFORMATION: Ikbkb-A-Forward primer

<400> SEQUENCE: 7
ccgcggtcga cgacaaggga aaactcaccg c                                   31

<210> SEQ ID NO 8
<211> LENGTH: 28
<212> TYPE: DNA
<213> ORGANISM: Artificial Sequence
<220> FEATURE:
<223> OTHER INFORMATION: Ikbkb-A-Reverse primer
```

<400> SEQUENCE: 8
cggggtaccg cagaggcgtg gaagcggg                                28

<210> SEQ ID NO 9
<211> LENGTH: 28
<212> TYPE: DNA
<213> ORGANISM: Artificial Sequence
<220> FEATURE:
<223> OTHER INFORMATION: Ikbkb-B-Forward primer

<400> SEQUENCE: 9
cggggtaccg gtggatatca tggcccag                                28

<210> SEQ ID NO 10
<211> LENGTH: 27
<212> TYPE: DNA
<213> ORGANISM: Artificial Sequence
<220> FEATURE:
<223> OTHER INFORMATION: Ikbkb-B-Reverse primer

<400> SEQUENCE: 10
cgcactagtg acgaaaggcc cggaagg                                 27

<210> SEQ ID NO 11
<211> LENGTH: 25
<212> TYPE: DNA
<213> ORGANISM: Artificial Sequence
<220> FEATURE:
<223> OTHER INFORMATION: Ikbkb-C-Forward primer

<400> SEQUENCE: 11
cgatatcgag acccctgact gcagc                                   25

<210> SEQ ID NO 12
<211> LENGTH: 26
<212> TYPE: DNA
<213> ORGANISM: Artificial Sequence
<220> FEATURE:
<223> OTHER INFORMATION: Ikbkb-C-Reverse primer

<400> SEQUENCE: 12
ggaattcacg ggcatccata ccttac                                  26

<210> SEQ ID NO 13
<211> LENGTH: 26
<212> TYPE: DNA
<213> ORGANISM: Artificial Sequence
<220> FEATURE:
<223> OTHER INFORMATION: Ikbkb-D-Forward primer

<400> SEQUENCE: 13
ggtggatcca ctagttctag agcggc                                  26

<210> SEQ ID NO 14
<211> LENGTH: 30
<212> TYPE: DNA
<213> ORGANISM: Artificial Sequence
<220> FEATURE:
<223> OTHER INFORMATION: Ikbkb-DM-Reverwe primer

<400> SEQUENCE: 14
ctcctgtcgg gcttgcttga tggcgatctg                              30

<210> SEQ ID NO 15
<211> LENGTH: 30

```
<212> TYPE: DNA
<213> ORGANISM: Artificial Sequence
<220> FEATURE:
<223> OTHER INFORMATION: Ikbkb-DM-Forward primer

<400> SEQUENCE: 15
catcaagcaa gcccgacagg agctcagccc                                         30

<210> SEQ ID NO 16
<211> LENGTH: 30
<212> TYPE: DNA
<213> ORGANISM: Artificial Sequence
<220> FEATURE:
<223> OTHER INFORMATION: Ikbkb-D-Reverse primer

<400> SEQUENCE: 16
cgtgcggccg cctctagaag cctccaggac                                         30
```

TRANSGENIC MODEL FOR DELAY-TYPE HYPERSENSITIVITY (DTH) AND USE THEREOF

CROSS-REFERENCE TO RELATED APPLICATIONS

The present application is a continuation-in-part application of a U.S. divisional patent application Ser. No. 14/455,951 filed Aug. 11, 2014, and also claims priority from a U.S. provisional patent application Ser. No. 62/038,375 filed Aug. 18, 2014, and the disclosure of which are incorporated herein by reference in their entirety.

FIELD OF INVENTION

The present invention refers to non-human transgenic mammals, preferably mice, which comprise a mutation in a genes encoding for IκB kinase β (IKK-β) protein. The present invention also provides methods for using these transgenic mammals as in vivo model in identifying and determining therapeutic or prophylactic activity of test compounds in delay-type hypersensitivity (DTH) and other inflammatory or cancerous diseases mediated by activation of IKK-$β^{C46A}$ mutants.

BACKGROUND OF INVENTION

Rheumatoid arthritis (RA), exemplary delay-type hypersensitivity (DTH) disease, is hard to be cured effectively, probably due to the differences of drug-sensitivity among patients' unique gene mutational background. Accordingly, personalized medicine would be the ultimate solution for tackling the drug-resistance problem and therefore, understanding the gene mutation profiling of patients would be a key for cocktailing the best personalized medicine protocol. COSMIC analysis showed that mutations on IκB kinase β (IKK-β) have been frequently reported in cancer patients that would probably lead to altered kinase activity, as well as serious immunological disorders such as deficiency of innate and acquired immunity. In addition, IKK-β plays a crucial role in the progression of inflammatory diseases and cancers, and therefore discovery of IKK-β inhibitors has become the most promising arena against inflammation and cancers. However, studies showed that mutations on existing drug binding sites, especially on cysteine residue, would abolish the kinase inhibitory effect of IKK-β inhibitor; because cysteine plays crucial role in protein's post-modification and functions. Accordingly, identification and characterization of IKK-β mutations especially on cysteine residues would be a key roadmap for understanding diseases pathogenesis and discovering personalized therapeutics.

Previously, it was reported a site directed mutagenesis in the genes encoding for IKK-β protein. Single point mutants with cysteine (C) residue replaced by alanine (A) includes C12A, C46A, C59A, C99A, C114A, C115A, C179A, C215A, C299A, C370A, C412A, C444A, C464A, C524A, C618A, C662A, C716A and C751A mutations. These site directed mutagenesis revealed that IKK-β C46A contributed to significantly increased kinase activity. To address the function of this mutant kinase in vivo, generating homozygous IKK-$β^{C46A}$ transgenic mice appears to be a promising in vivo model for examining inflammatory responses and anti-inflammatory potency of relevant agents.

In the presence of a mouse model carrying C46A mutation in IKK-β protein, it will enable a better characterization of the clinical phenotype, the pathogenetic mechanisms thereof, and to gather insights on possible novel therapies of DTH and other inflammatory or cancerous diseases mediated by this mutant protein.

SUMMARY OF INVENTION

The present invention provides non-human transgenic mammals, preferably mice, which comprise a mutation in the genes encoding IκB kinase β (IKK-β) and the product expressed thereby for regulating IKK-β and NF-κB signaling.

The transgenic mammals of the present invention comprise a single point mutation in the amino acid sequence at a cysteine residue being replaced by alanine in the IKK-β protein such that the protein kinase activity will be insensitive to the suppression of the compound, which target IKK-β via this particular cysteine residue. The single point mutation in the present transgenic mammals is at amino acid residue 46 which is a cysteine in wild-type and the mutation becomes C46A in the IKK-β protein. If a compound can specifically bind to this mutated C46A, it can inhibit the activation of said signaling pathway which potentially leads to more severe inflammatory response or cancerous diseases.

The present invention also provides a method for generating the transgenic mammals carrying the C46A mutation in the IKK-β protein. In one embodiment, the present invention provides a vector for targeting the IKK-β gene. The vector which can be a linearized targeting construct carries a mutated exon 3 at nucleotides 32 and 33 of the coding sequence of Ikbkb gene. The linearized targeting construct containing TG to GC transversion mutation at nucleotides 32 to 33 determines the amino acid change Cys46Ala (C46A).

According to a further embodiment, the IKK-β mutants are validated by PCR and gene sequencing using two pairs of forward and reverse primers. One pair is used to validate the 5'arm while another pair is used to validate 3'arm of the Ikbkb gene.

The present invention further provides a method for identifying and determining therapeutic or prophylactic activity of a test compound in DTH and other inflammatory or cancerous diseases mediated by activation of IKK-$β^{C46A}$ mutant protein. Measures of one or more physiological, morphological, molecular and/or histological parameter(s) are taken after said test compound is administered to the transgenic mice, and compared the measures with measures obtained from control mice. If the test compound targets Cysteine 46, the compound would fail to bind and inhibit activation of IKK-$β^{C46A}$ mutant protein as a result of Cysteine 46 binding site being mutated to Alanine according to an embodiment of the present invention. In contrast, if the test compound can target IKK-β via other drug binding sites, but not on cysteine 46 residue, the activation of IKK-$β^{C46A}$ and NF-κB signaling pathway can be suppressed.

In yet another embodiment, the inflammatory or cancerous diseases are selected from a group consisting of arthritis, delay-type hypersensitivity (DTH) autoimmune disease and various types of cancer with different origin, which are mediated by activation IKK-$β^{C46A}$ mutant protein.

The transgenic mice of the present invention are useful in cross-breeding experiments in order to gather further pathophysiological insights on possible novel therapies and treatments of DTH and other inflammatory or cancerous diseases, which are mediated by activation of IKK-$β^{C46A}$ mutant protein.

DETAILED DESCRIPTION OF THE PREFERRED EMBODIMENTS

Figure 1:
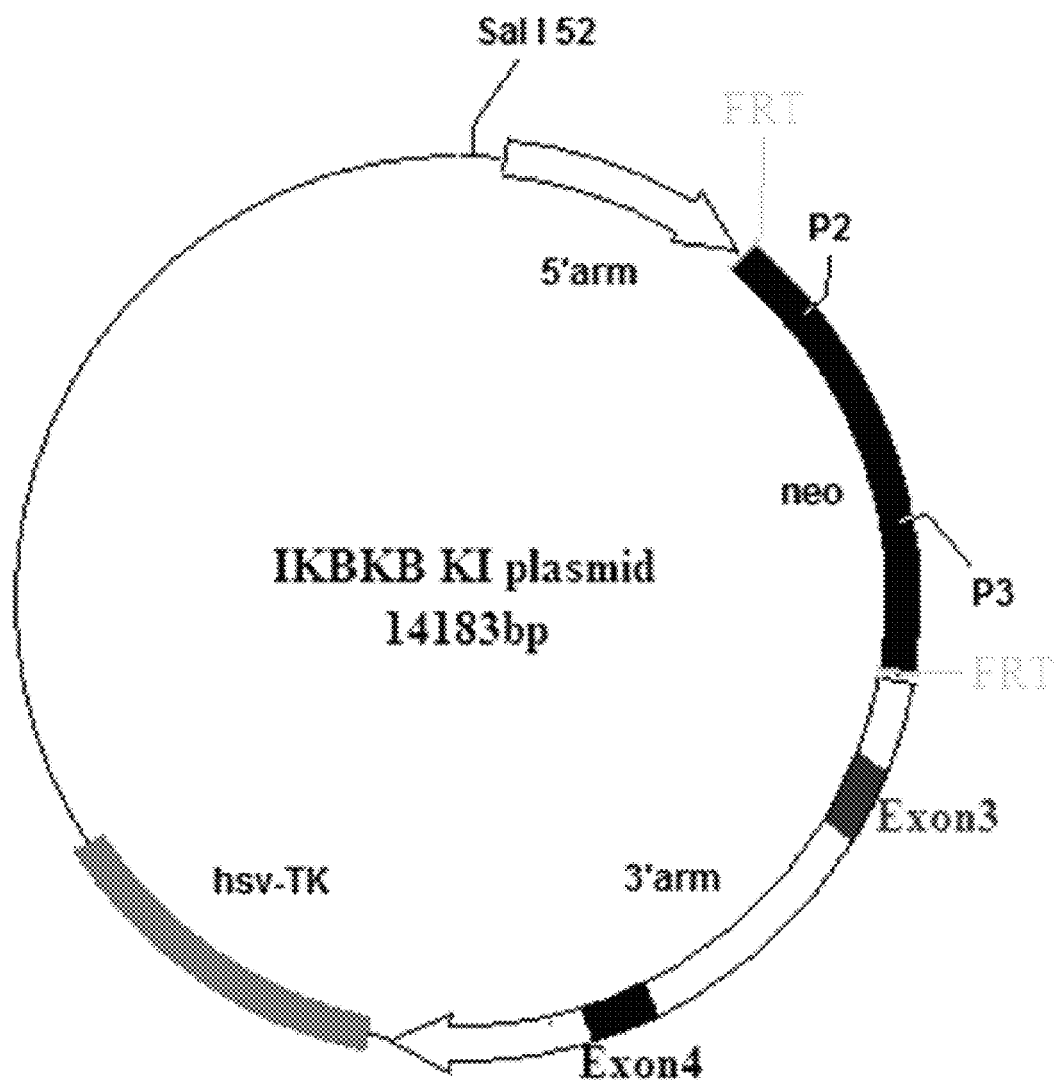
FIG. 1 shows a schematic representation of the genomic map of IKK-β gene knockin vector according to an embodiment of the present invention.

As used herein and in the claims, "comprising" means including the following elements but not excluding others.

The present invention refers to non-human transgenic mammals, preferably mice, which comprise a mutation in the genes encoding for the IKK-β protein. These transgenic animals are used as in vivo models in determining therapeutic or prophylactic activity of test compounds in delay-type hypersensitivity (DTH) and other inflammatory or cancerous diseases mediated by IKK-$β^{C46A}$ mutants.

This transgenic mouse can be applied to provide insight on the regulatory mechanisms of IKK-β in various inflammatory and cancerous responses, as well as novel indications for personalized drug discovery.

The following preparations and examples are given to enable those skilled in the art to more clearly understand and to practice the present invention. They should not be considered as limiting the scope of the invention, but merely as being illustrative and representative thereof.

Example 1

This example describes the generation of the mutated gene and targeting vector used in a transgenic mouse model of the present invention.

The targeting vector is designed based on the Ikbkb genomic sequence obtained from the Ensembl database (http://www.ensembl.org/index.html). Mouse Ikbkb-001 transcript consists of 22 exons. According to the bioinformatic analysis, the mutation sites are located in exon 3. FRT-neo-FRT template is designed in the construct to allow neomycin selection. The site mutations would result in Cys46Ala (C46A) mutation. The targeting vector containing T-G to G-C transversion mutation at nucleotides 32 and 33 in exon 3 of Ikbkb gene is achieved by ET cloning.

Four little homology arms, A, B, C and D, are amplified by PCR using BAC plasmid as the template. There are five pairs of forward and reverse primers for constructing these four little homology arms which are listed in Table 2. Homology arms A and B are inserted into SalI-SpeI sites of pBR322-2S to obtain the vector for retrieving. Linearization vector by KpnI is transformed into BAC bacterium. The Retrieve vector, containing DNA sequences ranging from A to B, which include 5'arm and 3'arm, is obtained from BAC plasmid by homologous recombination and ampicillin screening. Homology arm C is inserted into EcoRV-EcoRI sites and D containing site mutations is inserted into BamHI-NotI sites of PL451 plasmid. Double digested by KpnI and NotI, the C-Neo-D fragment is isolated from the vector and knocked into the Retrieve vector by homologous recombination, thus obtaining the targeting vector pBR322-MK-Ikbkb-KI (SEQ ID NO: 1), which is evaluated by restriction endonucleases and sequencing.

The obtained targeting vector is evaluated by restriction endonucleases and sequencing, confirming the insertion of the homologous arms and their direction. The five pairs of forward and reverse primers used to construct or confirm the insertion correspond to SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15 and SEQ ID NO: 16, respectively.

Conclusion.

The circle map of the targeting vector is shown in FIG. 1 and the features are summarized in Table 1.

TABLE 1

The locations marked in IKBKB-KI plasmid. 5947-5948: TG-GC transversion mutation at nucleotides 32 and 33 in exon 3 of Ikbkb gene.
Ikbkb-KI vector

| Start | End | Length | Name |
|---|---|---|---|
| 58 | 3867 | 3810 | 5' arm |
| 3868 | 5876 | 1949 | Neo |
| 4342 | 4322 | 21 | P2 |
| 5480 | 5505 | 24 | P3 |
| 5817 | 8372 | 2556 | 3' arm |
| 8373 | 57 | 5868 | pBR322-TK |

TABLE 2

Forward and reverse primers for constructing or confirming insertion of homology arms of the Ikbkb gene

| Name of Primer | Nucleotide Sequence | SEQ ID NO |
|---|---|---|
| Ikbkb-A-F | CCGCGGTCGACGACAAGGGAAAACTCACCGC | 7 |
| Ikbkb-A-R | CGGGGTACCGCAGAGGCGTGGAAGCGGG | 8 |
| Ikbkb-B-F | CGGGGTACCGGTGGATATCATGGCCCAG | 9 |
| Ikbkb-B-R | CGCACTAGTGACGAAAGGCCCGGAAGG | 10 |
| Ikbkb-C-F | CGATATCGAGACCCCTGACTGCAGC | 11 |
| Ikbkb-C-R | GGAATTCACGGGCATCCATACCTTAC | 12 |
| Ikbkb-D-F | GGTGGATCCACTAGTTCTAGAGCGGC | 13 |

TABLE 2-continued

Forward and reverse primers for constructing or confirming insertion of homology arms of the Ikbkb gene

| Name of Primer | Nucleotide Sequence | SEQ ID NO |
|---|---|---|
| Ikbkb-DM-R | CTCCTGTCGGGCTTGCTTGATGGCGATCTG | 14 |
| Ikbkb-DM-F | CATCAAGCAAGCCCGACAGGAGCTCAGCCC | 15 |
| Ikbkb-D-R | CGTGCGGCCGCCTCTAGAAGCCTCCAGGAC | 16 |

Example 2

This example describes the preparation and generation of the IKK-$\beta^{C46A}$ transgenic mice model.

ES Cell Electroporation for DNA Transfer.

Exponentially growing ES cells are digested with 0.125% trypsin-EDTA and counted. Cell suspension is adjusted to a final concentration of 1.5×107 cells/ml by adding an appropriate amount of PBS. Mix together 0.8 ml ES cell suspension and 35 µg NotI linearized pBR322-MK-Ikbkb-KI vector (FIG. 2) in a sterile electroporation cuvette and electroporation. The eletroporator is set to 240 V/500 µf. Resuspend ES cells and allocate on average onto three feeder cell seeded 10 cm dish.

Positive and Negative Drug Selection.

ES cells are selected in medium containing G418 (300 mg/L) and ganciclovir (2 µmol/L) 24 h and 48 h after electroporation, respectively. Medium is changed daily and clones can be picked after 7-8 days of culture when resistant ES cells grow into visible clones.

Picking and Culture of Double Resistant ES Cell Clones.

Resistant clones are picked and digested in 96-well plate (U bottom) containing 30 µl 0.1% trypsin-EDTA per well for 3 min. Cells are dispersed by gentle agitation and transferred to 96-well culture plates. The majority of the cells are cryopreserved when cells reach 60-80% confluence and the remaining cells are allowed to grow to 100% confluence and used for genomic DNA extraction.

ES Cell Genomic DNA Extraction.

Aspirate the medium from the well and add 80 µl lysis buffer containing 1 g/L proteinase K. After overnight digestion at 56° C., add anhydrous ethanol and extract DNA following conventional method and DNA is dissolved in 100 µl TE buffer.

PCR Genotyping of Homologous Recombinant Clones.

Figure 2:
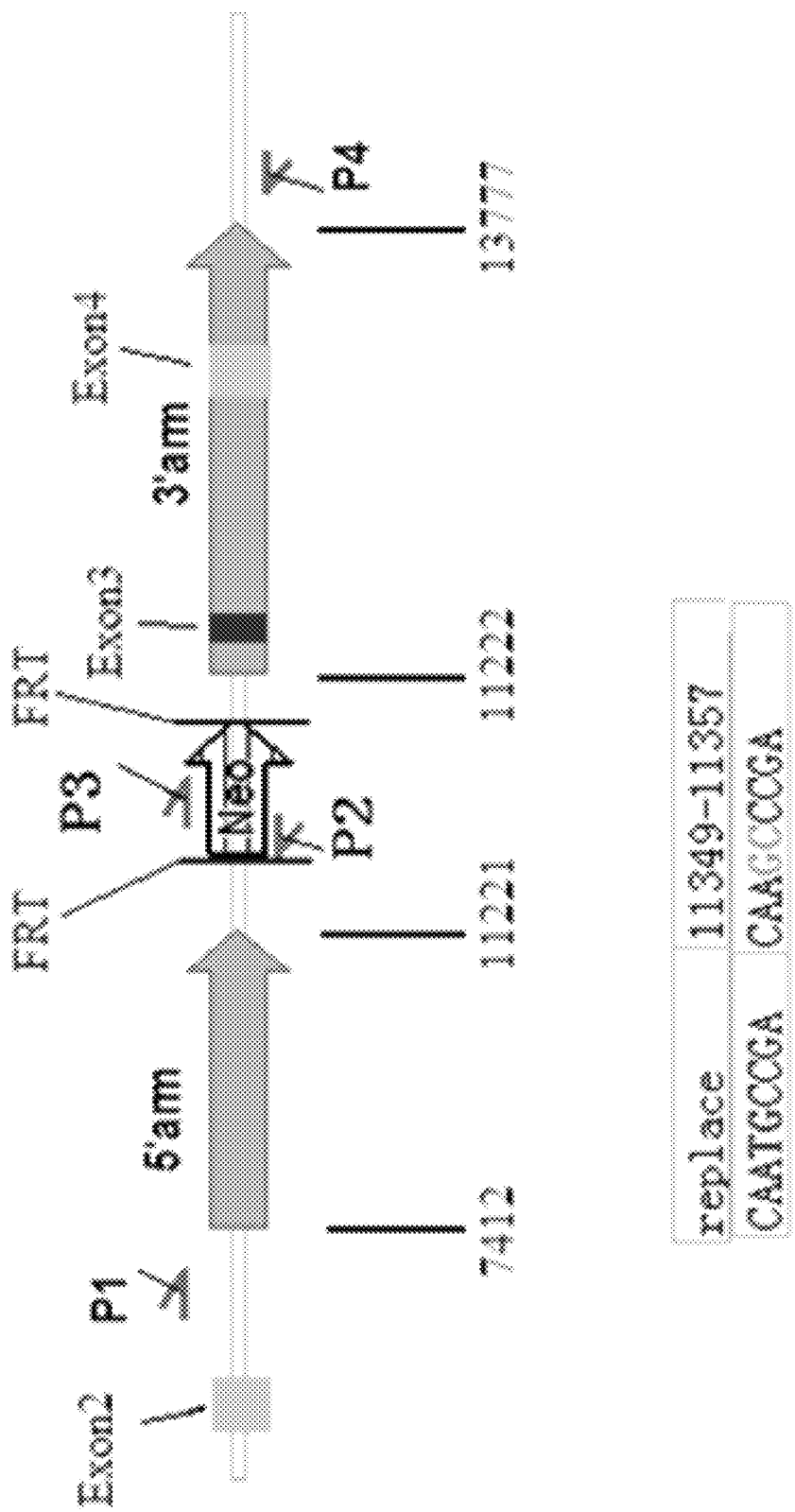
FIG. 2 illustrates targeting strategy for Ikbkb gene knockin. The targeting vector contains homology arms of 3.8 kb (5'arm) and 2.5 kb (3'arm). The mutation sites are located in exon 3, where nucleotides TG are changed to GC.

As shown in FIG. 2, primers ES-5-up (SEQ ID NO: 3) and ES-3-low (SEQ ID NO: 6) are designed at the regions upstream 5'arm and downstream 3'arm, respectively, while primers ES-5-low (SEQ ID NO: 4) and ES-3-up (SEQ ID NO: 5) are designed within the neo sequences. ES-5-up and ES-5-low are used to evaluate the recombination on the 5'arm, with the following conditions: 94° C. for 5 min and 35 cycles of 94° C. for 30 sec, 60° C. for 25 sec, 65° C. for 5 min, and 10 min incubation at 72° C. at the end of the run. A 4.4 kb fragment should be amplified in positive clones. The enzyme used is NEB longamp taq (M0323S), and the reaction mixture is set up following the manufacturer's instruction. On the other hand, ES-3-up and ES-3-low are used to evaluate the recombination on the 3'arm, with the following conditions: 94° C. for 5 min and 35 cycles of 94° C. for 30 sec, 68° C. for 3 min, and 10 min incubation at 72° C. at the end of the run. A 3.2 kb fragment should be amplified in positive clones. The enzyme used is La Taq (TaKaRa, RR02MB), and the PCR buffer is 10×La buffer II. The reaction mixture is following the manufacturer's instruction.

Figure 3:
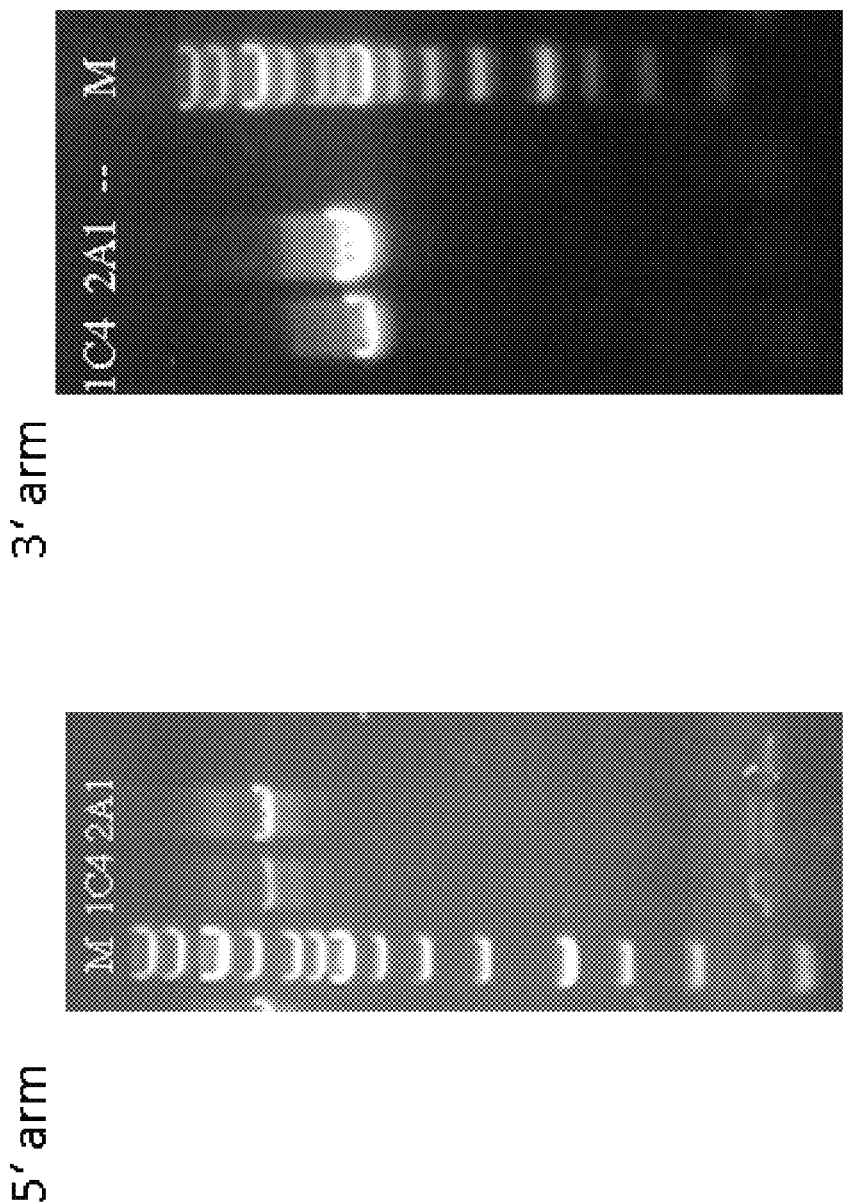
FIG. 3 shows the size of PCR products at 5' and 3' arm of two positive ES cell clones (1C4 and 2A1) identified by gel electrophoresis; M: 1 kb DNA ladder (Fermantas, SM1163).

During ES cell electroporation, the actual voltage and the discharge time are 256 V and 10.2 ms, respectively. 96 resistant clones are obtained. After extraction of the genomic DNA from ES cells in 96-well plate, positive clones are screened by PCR. Two clones (1C4 and 2A1) were identified in FIG. 3. PCR products of 5'arm and 3'arm are recovered with gel extraction kit and sequenced (5'arm: nucleotide 58-3867; 3'arm: nucleotide 5817-8372 in SEQ ID NO: 1), indicating that clones 1C4 and 2A1 have undergone correct homologous recombination. They are used in the subsequent blastocyst microinjection and embryo transfer.

Blastocyst Microinjection of ES Cells and Embryo Transfer.

DMEM complete medium without LIF is used during blastocyst microinjection. About 15 ES cells are injected into each blastocyst and the injected blastocysts are incubated in DMEM complete medium without LIF at 37° C., 5% $CO_2$ for about 1 h before they are transplanted into the uterine horns of 2.5-day-postcoitum pseudopregnant females, with 8-10 embryos per side. The pseudopregnant recipient mice are bred in the SPF animal house of Shanghai Research Center for Model Organisms and are allowed to deliver chimeric offspring naturally.

Figure 4:
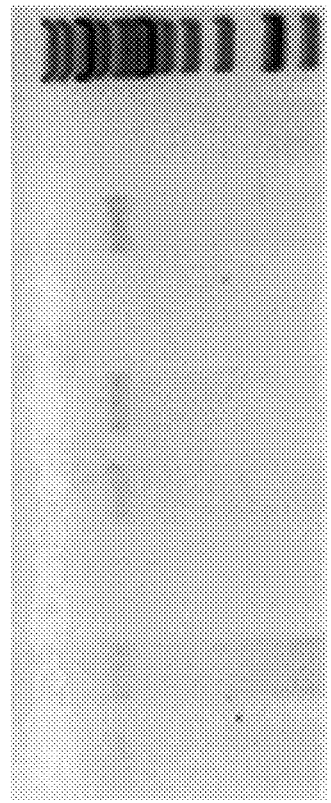
FIG. 4 shows the size of PCR products of eight heterozygous F1 mice (lanes 1 to 8) identified by gel electrophoresis; WT: wild type; M: 1 kb DNA ladder (Fermantas, SM1163).
Figure 4:
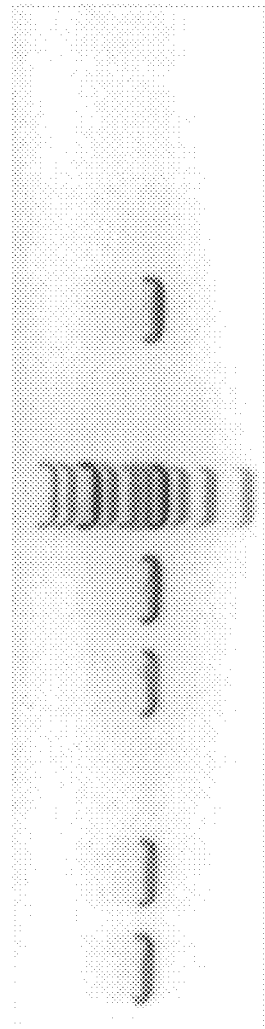

Chimeric Mice Breeding and PCR Genotyping:

Chimeric males with more than 50% coat color chimerism are selected and mated with pure C57BL/6J females to produce mice with white-bellied agouti coat, which are originated from the injected ES cells. Finally, five heterozygous mice are identified by PCR using the same method as in ES cell genotyping in FIG. 4.

Example 3

This example describes the in vitro and in vivo kinase activity and the inflammatory response of Cys-46 IKK-β mutant.

IKK-β Kinase Assay.

IKK-β kinase assay is performed using a K-LISA™ IKKβ-Inhibitor Screening Kit (Calbiochem).

Delay-Type Hypersensitivity Test and Immunohistochemical Staining.

The in vivo anti-inflammatory effect of a well-known IKK-β inhibitor, DMY, is examined by administering this inhibitor to a mouse with delay-type hypersensitivity (DTH) induced based on the previously described method. The ear samples of DTH mice are fixed in 4% neutral-buffered formalin. Each sample is cut longitudinally into half and embedded in paraffin (Panreac), and then cut into 5 µm sections.

Figure 5A:
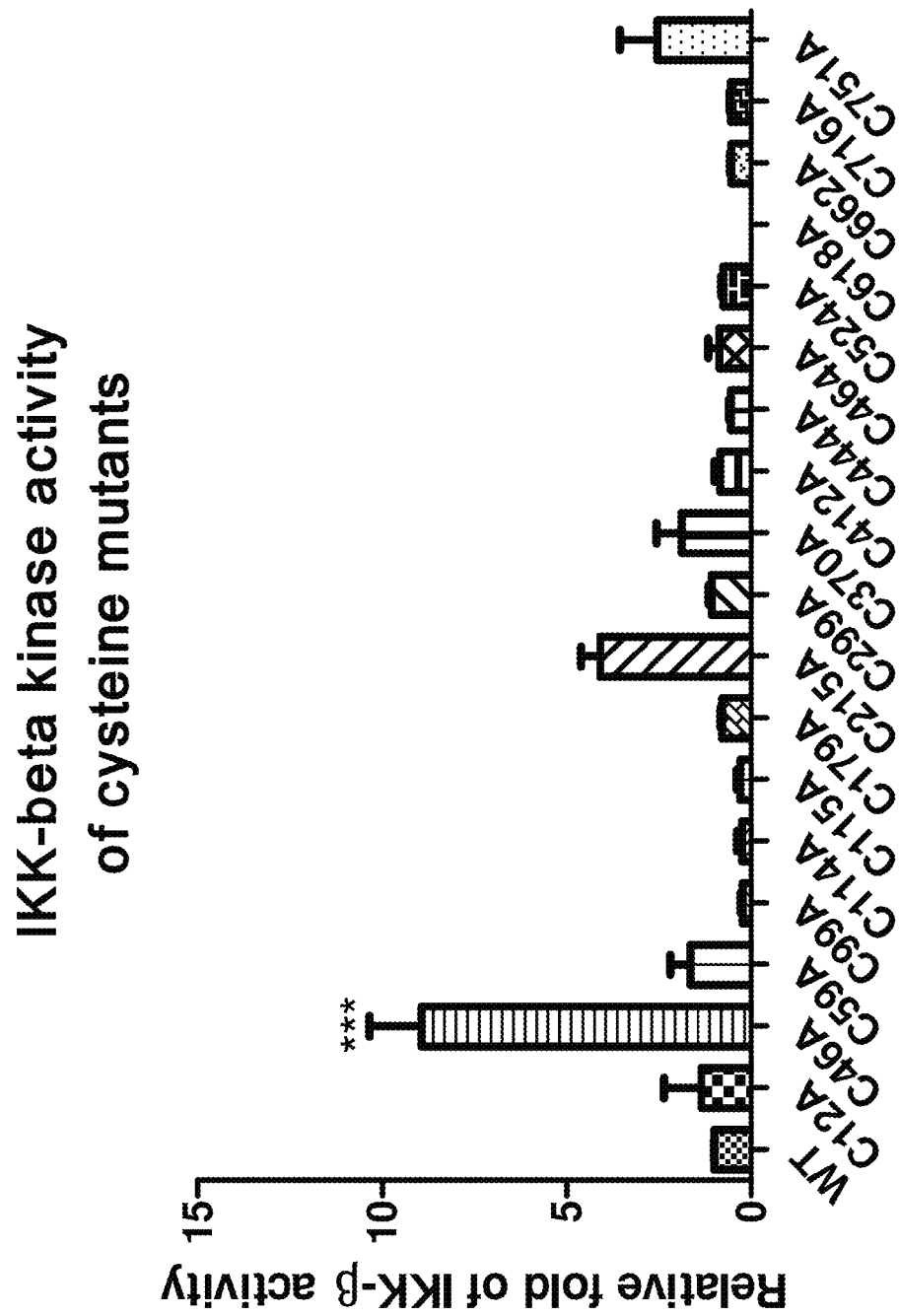
FIG. 5a shows a stronger IKK-β kinase activity of cysteine 46 mutant among other cysteine IKK-β mutants.
Figure 5B:
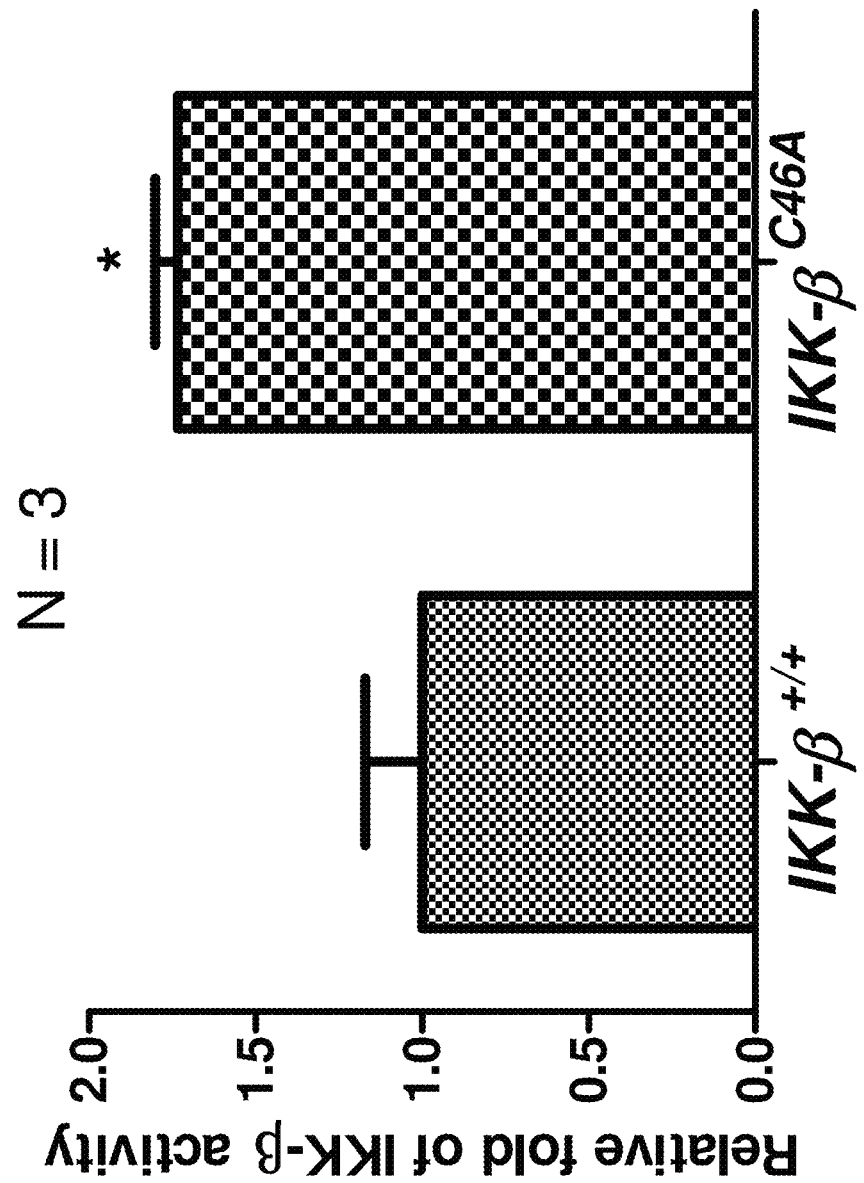
FIG. 5b shows a stronger IKK-β kinase activity of IKK-β protein isolated from kidney tissue of IKK-$β^{C46A}$ mutant mice compared to IKK-$β^{+/+}$ wild-type mice.
Figure 5C:
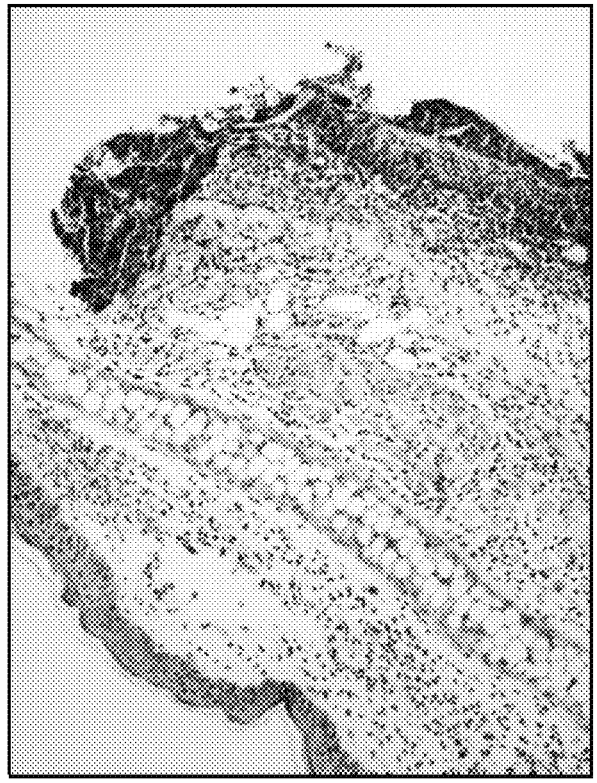
FIG. 5c shows a stronger inflammatory response in the ear tissues dissected from IKK-$β^{C46A}$ mutant mice compared to IKK-$β^{+/+}$ wild-type mice.
Figure 5C:
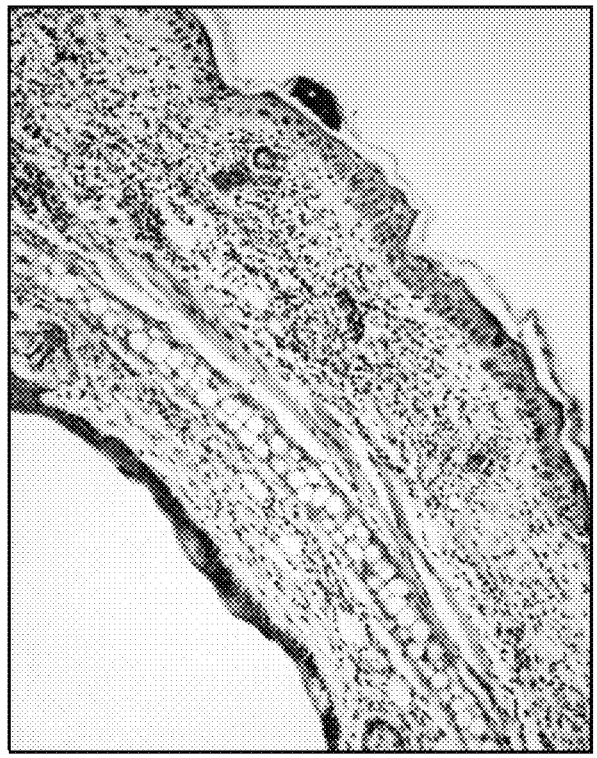

Results:

Site-directed mutagenesis reveals that mutation of IKK-β cysteine-46 to alanine (C46A) contributes to the most significantly increased kinase activity as compared to mutation in other cysteine residues (FIG. 5a). To address the function of this specific mutant kinase in vivo, homozygous IKK-$\beta^{C46A}$ transgenic mice are generated. Their inflammatory responses to dinitrofluorobenzene (DNFB), an agent inducing delay-type hypersensitivity, and the anti-inflammatory potency of relevant agents are examined immunohistochemically. Immuno-precipitated IKK-β protein from kidney tissues of IKK-$β^{C46A}$ mutant mice show a markedly increased kinase activity compared to an equal amount of tissues from IKK-$β^{+/+}$ animals (FIG. 5b). Concomitantly, homozygous IKK-$β^{C46A}$ mutant mice challenged with DNFB display a stronger inflammatory response by increasing the number of ear edema shown in H&E staining of ear tissue compared to that in IKK-$β^{+/+}$ animal (FIG. 5c).

Conclusion:

These findings indicate a stronger kinase activity and enhanced inflammatory response in homozygous IKK-$β^{C46A}$ mutant mice.

Example 4

This example describes an in vitro study to verify that cysteine 46 is a specific drug binding site on IKK-β for regulation of IKK-β and NF-βB signaling.

IKK-β Kinase Assay.

IKK-β kinase assay is performed using a K-LISA™ IKKβ-Inhibitor Screening Kit (Calbiochem).

Western Blotting Analysis.

IKK-$β^{-/-}$ deficient mouse embryonic fibroblasts (MEFs) are provided as a gift by Prof. Michael Karin (University of California, San Diego). IKK-$β^{-/-}$ deficient MEFs transfected with IKK-β wild-type or mutant C46A constructs are pretreated with DMY at 37° C. for 60 min, and then the cells are stimulated with TNF-α and harvested for western blotting analysis. The expressions of IκBα, p-$p65^{ser536}$, FLAG-IKK-β and actin are detected with their specific antibodies.

Figure 6A:
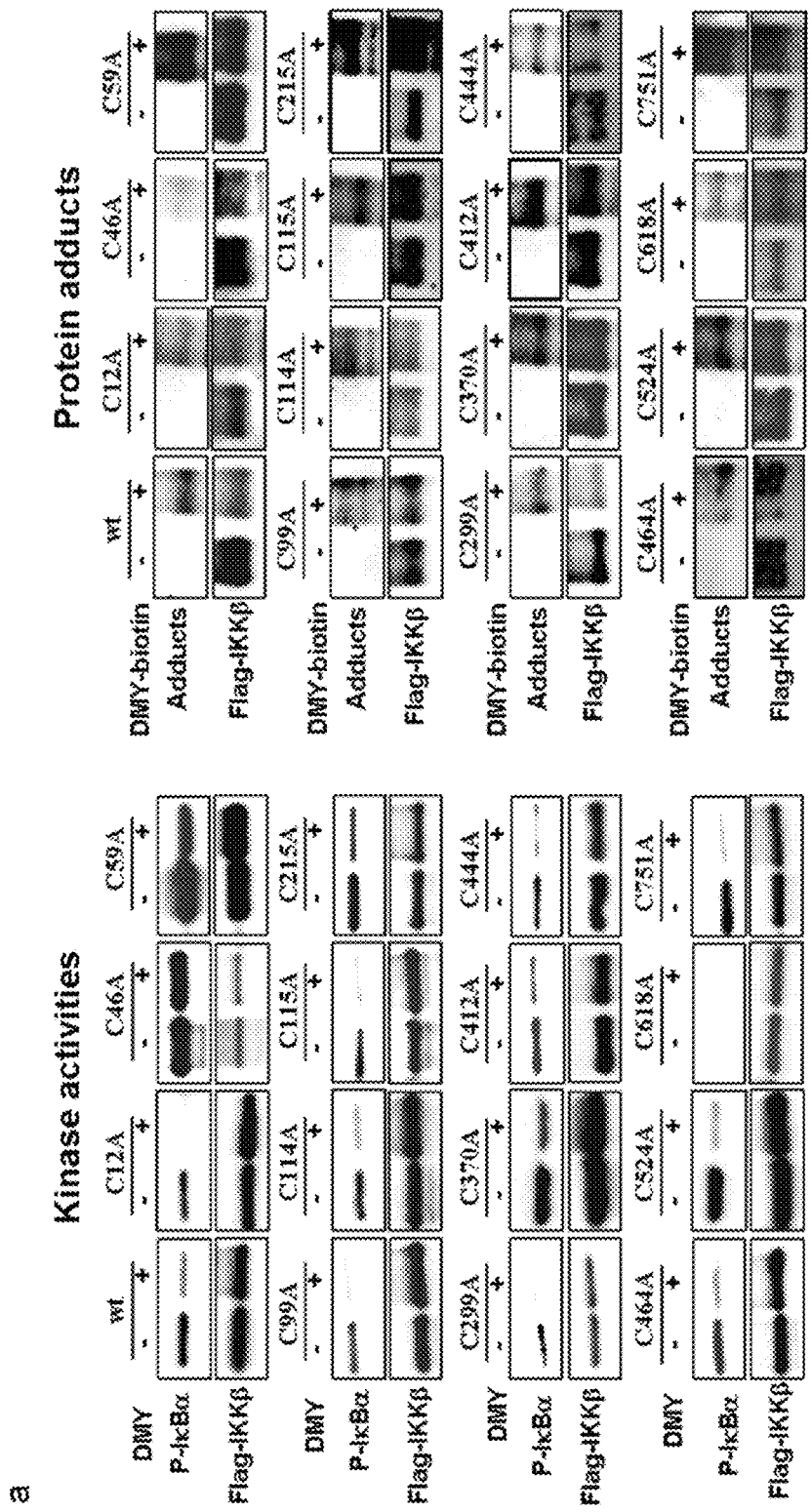
FIG. 6a, FIG. 6b and FIG. 6c show that the cysteine 46 residue of IKK-β is a specific drug binding site for DMY to suppress IKK-β-NF-κB signaling.
Figure 6B:
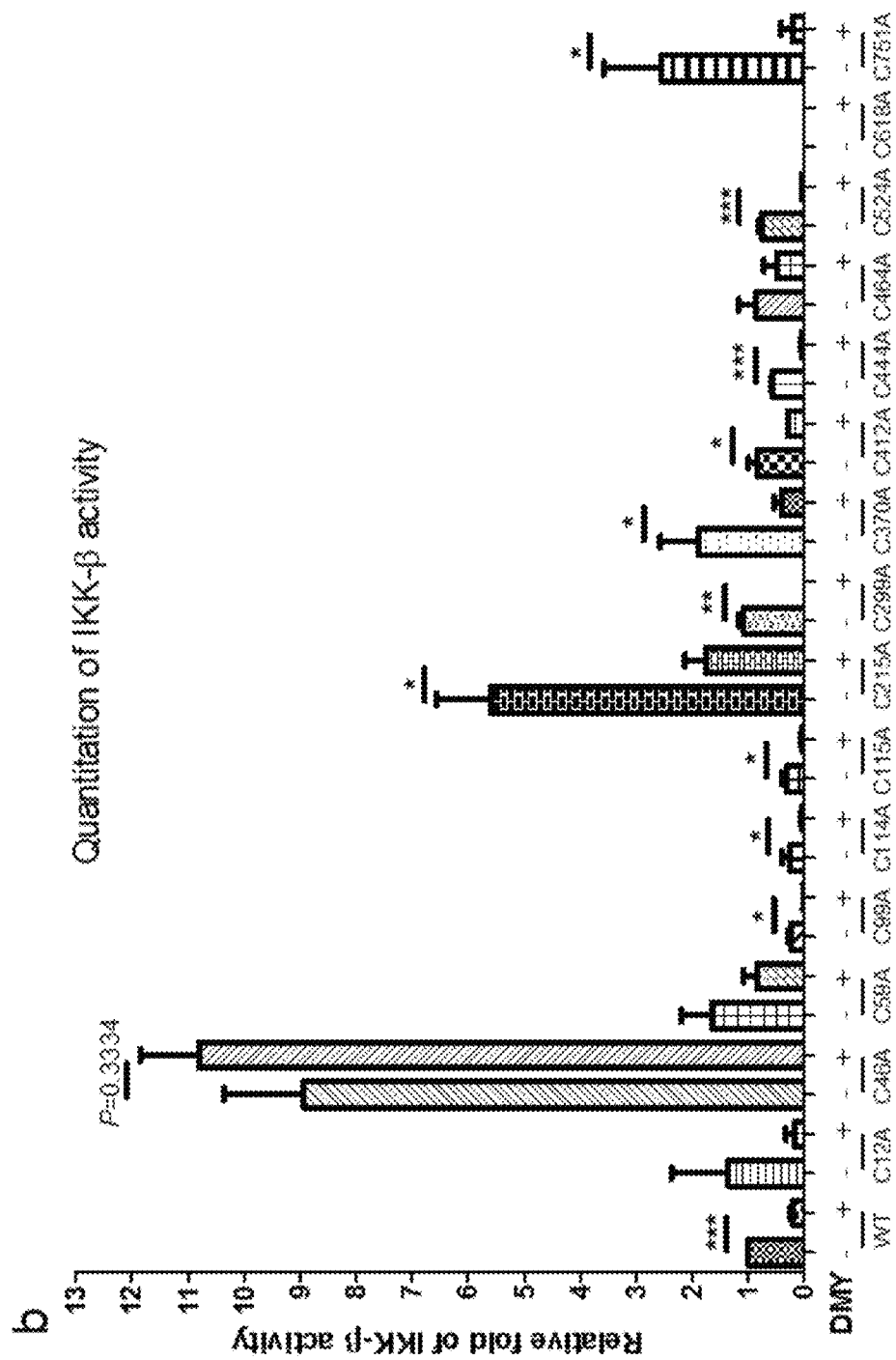
Figure 6C:
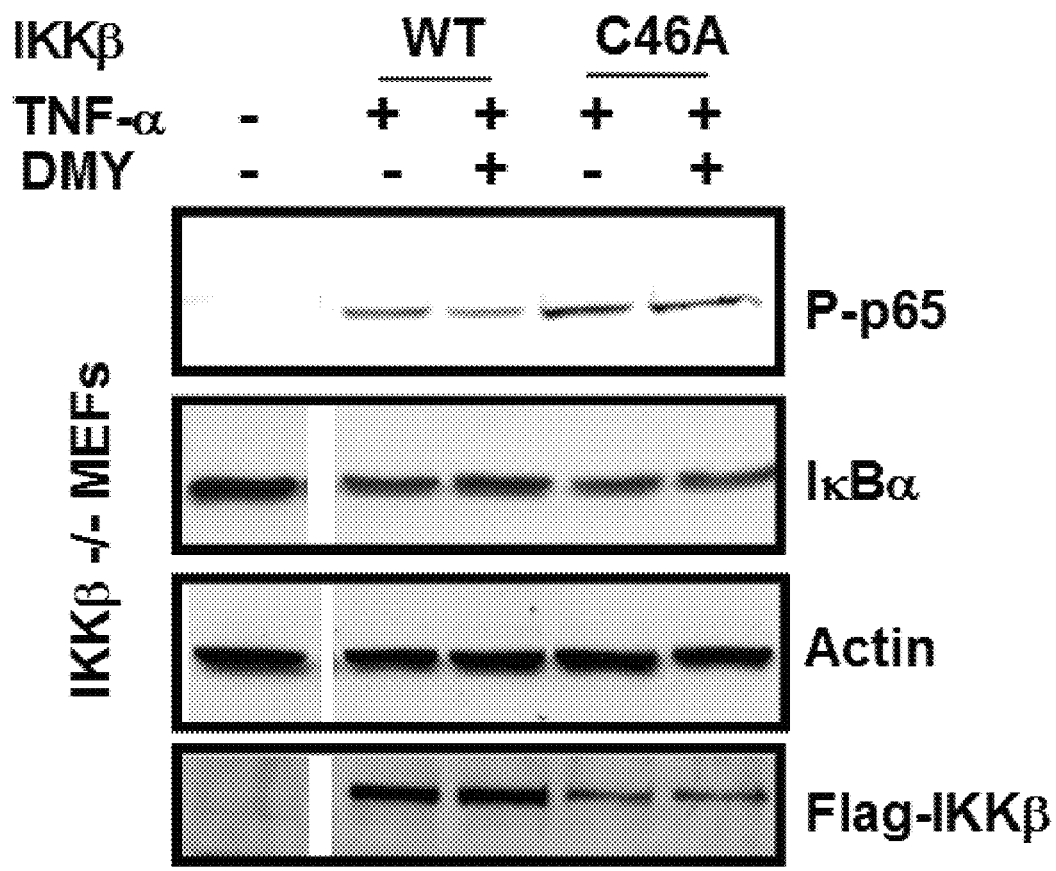

Results:

To determine the specificity to which cysteine residue(s) on IKK-β for the inhibitory action of a well-known inhibitor, DMY, all other 15 single point mutation IKK-β constructs with cysteine (C) residues are replaced with alanine (A) by site-directed mutagenesis (FIG. 6a), except Cys-46. This example shows that except C618A, all other mutants retain their kinase activities as determined by phosphorylation of IκBα. Importantly, mutation on Cys-46 residue (C46A) of IKK-β abrogates the kinase inhibitory effect of DMY and inhibited the protein adducts formation with DMY-biotin (FIGS. 6a & b), whereas C46A mutant IKK-β demonstrates a significant increase in kinase activities compared to its wild-type IKK-β. Using the IKK-$β^{-/-}$ MEFs, it is verified that Cys-46 residue on IKK-β is crucial for the DMY-mediated suppression of NF-κB signaling as determined by the suppression of TNF-α-induced phosphorylation of NF-κB p65 and degradation of IκBα in IKK-$β^{-/-}$ MEFs transfected with IKK-β (wt), but not with IKK-β (C46A) mutant (FIG. 6c).

Conclusion:

Collectively, Cys-46 is verified as a functional cysteine residue as well as specific drug binding site in regulating kinase activity of IKK-β and its in vivo inflammatory response.

Example 5

This example describes the diminished anti-inflammatory effect of DMY as determined by the population of CD4$^+$ and CD8$^+$ T lymphocytes in the ear tissues of DTH-IKK-$β^{+/+}$ wild type and -IKK-$β^{C46A}$ mutant mice.

Delay-Type Hypersensitivity Test and Immunohistochemical Staining.

The in vivo anti-inflammatory effect of DMY on CD4$^+$ and CD8$^+$ lymphocytes is examined by administering this inhibitor to the mouse with delay-type hypersensitivity (DTH) based on the previously described method. The ear samples of DTH mice are fixed in 4% neutral-buffered formalin. Each sample is cut longitudinally into half and embedded in paraffin (Panreac), and then cut into 5 μm sections. Immunohistochemical staining is performed on slides.

Figure 7:
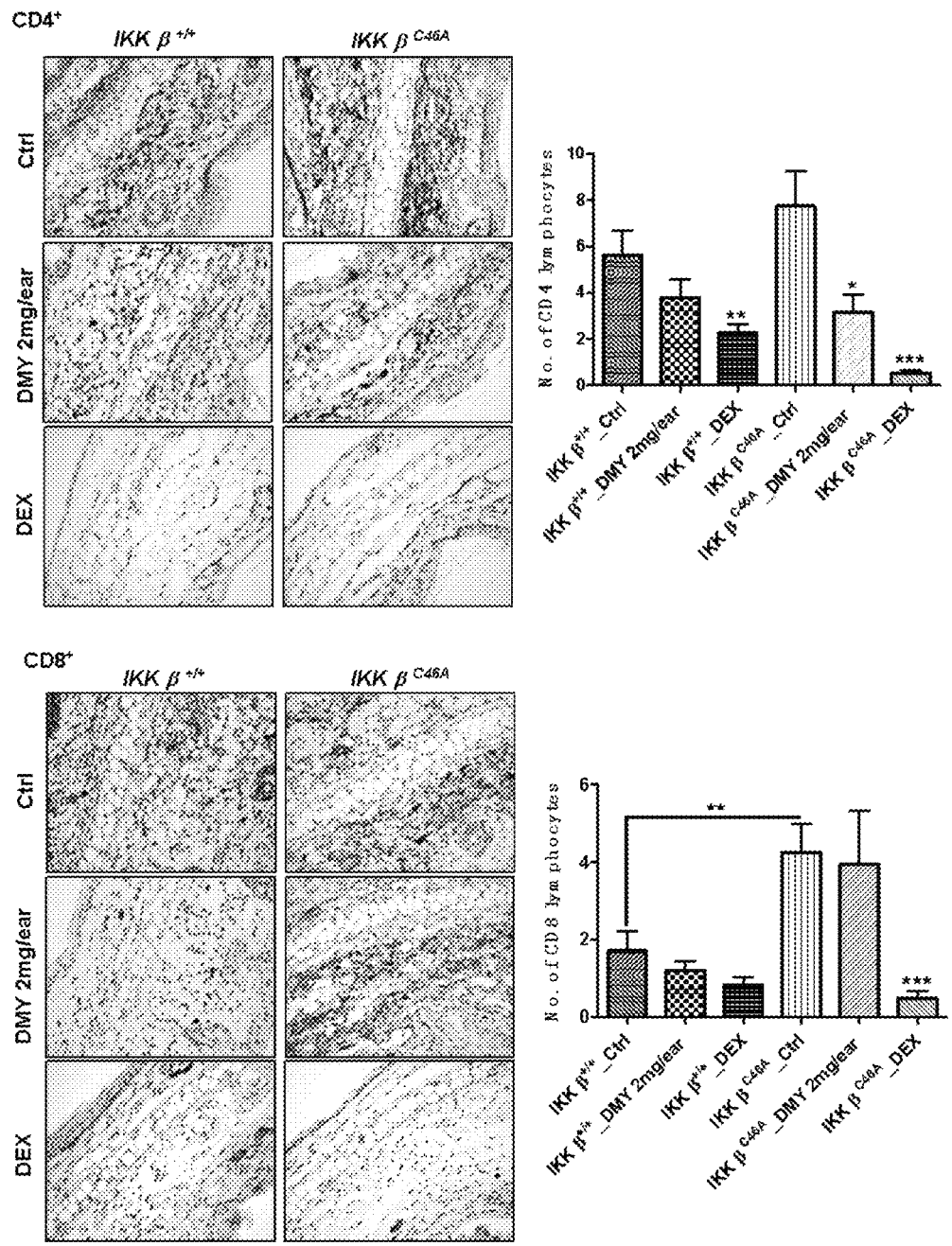
FIG. 7 shows a diminished anti-inflammatory effect of DMY as determined by the population of $CD4^+$ and $CD8^+$ T lymphocytes in the ear tissues of DTH-IKK-$β^{+/+}$ wild type and -IKK-$β^{C46A}$ mutant mice.

Results:

The effector CD4$^+$ and CD8$^+$ lymphocytes, which mediate DNFB-induced DTH, are consistently increased in number in the ear sections of DNFB-treated IKK-$β^{C46A}$ mutant mice compared to IKK-$β^{+/+}$ mice. In DMY-treated animals, the number of CD8$^+$ lymphocytes gradually decreases in IKK-$β^{+/+}$ mice, but not in IKK-$β^{C46A}$ mutant mice (FIG. 7), suggesting that CD8$^+$ lymphocytes are the major immuno-component cell population for the anti-inflammatory action of DMY in wild-type but not in IKK-$β^{C46A}$ mutant mice.

Conclusion:

These findings suggest that IKK-$β^{C46A}$ mutant mice show higher inflammatory potency and is less sensitive to the anti-inflammatory effect of DMY compared to IKK-$β^{+/+}$ wild-type mice.

Example 6

This example describes an in vivo study to demonstrate the anti-inflammatory effect of DMY on Collagen-II induced arthritis (CIA) rat model.

Experimental arthritis induced by collagen-II in rats. CIA is induced in female Wistar rats. Dexamethasone (DEX, 0.1 mg/kg), methotrexate (MTX, 3.75 mg/kg, twice per week) and indomethacin (Indo, 1 mg/kg) are used as reference drugs.

Figure 8A:
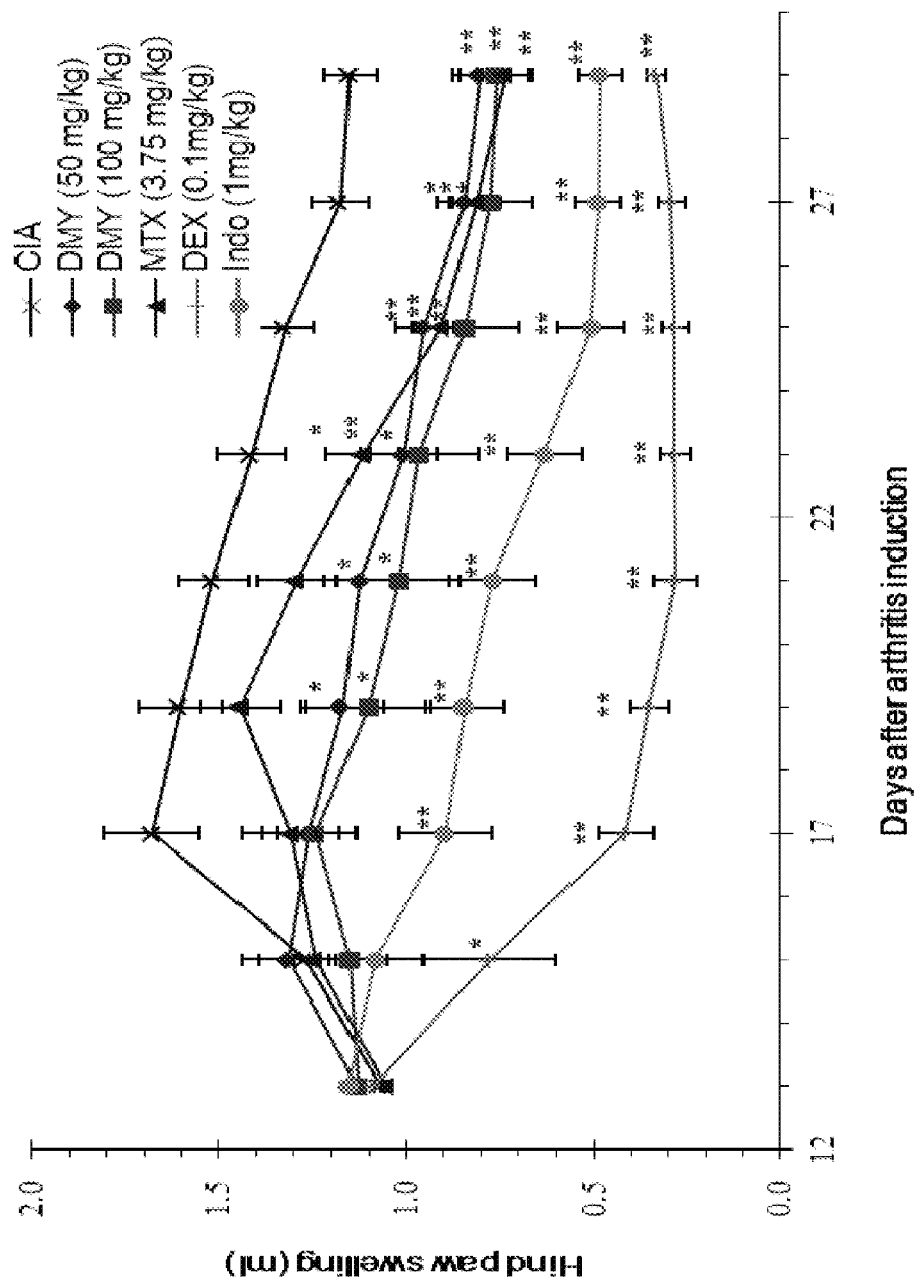
FIG. 8a, FIG. 8b, FIG. 8c, FIG. 8d and FIG. 8e show that DMY exhibits potent anti-inflammatory effect on CIA rat model via suppression of NF-κB signaling.
Figure 8B:
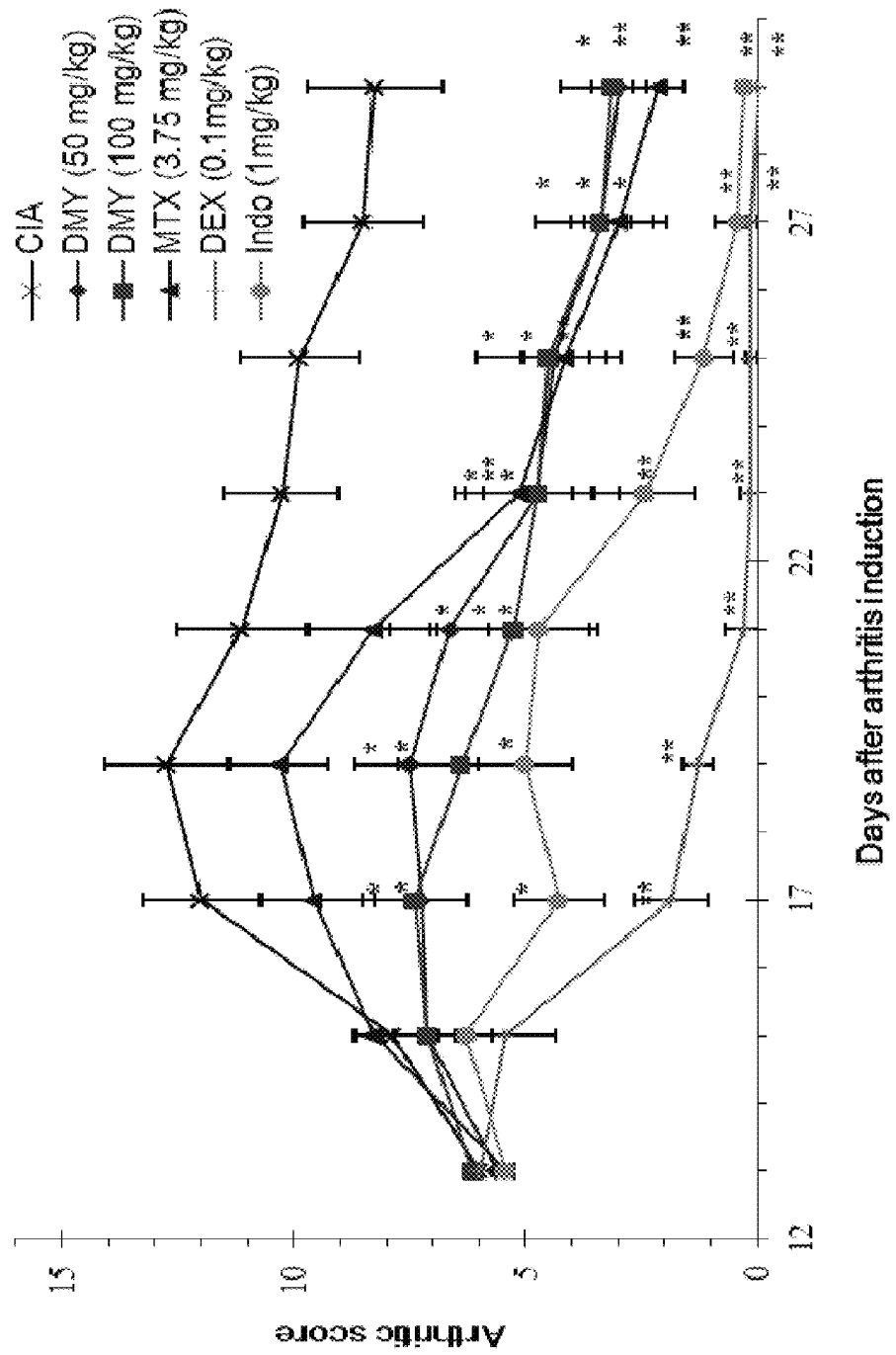
Figure 8C:
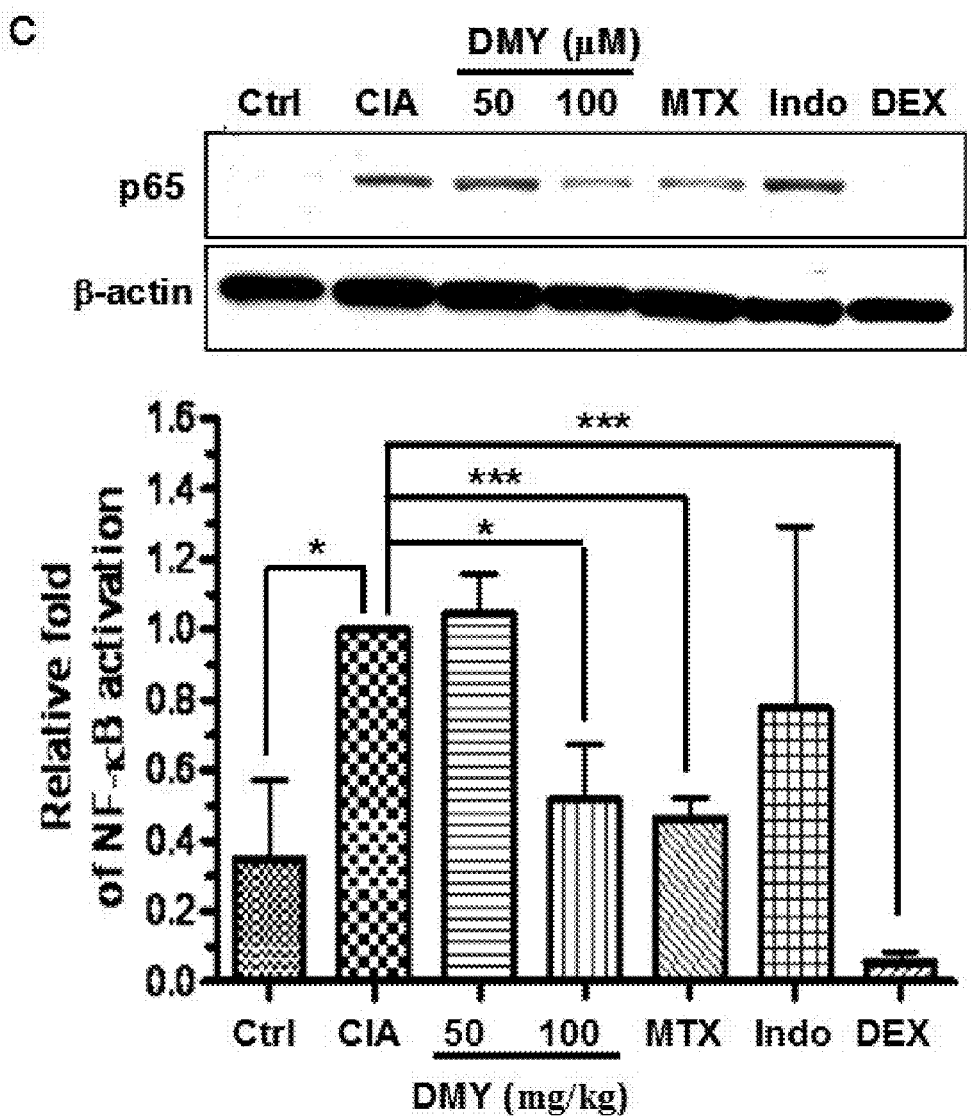
Figure 8D:
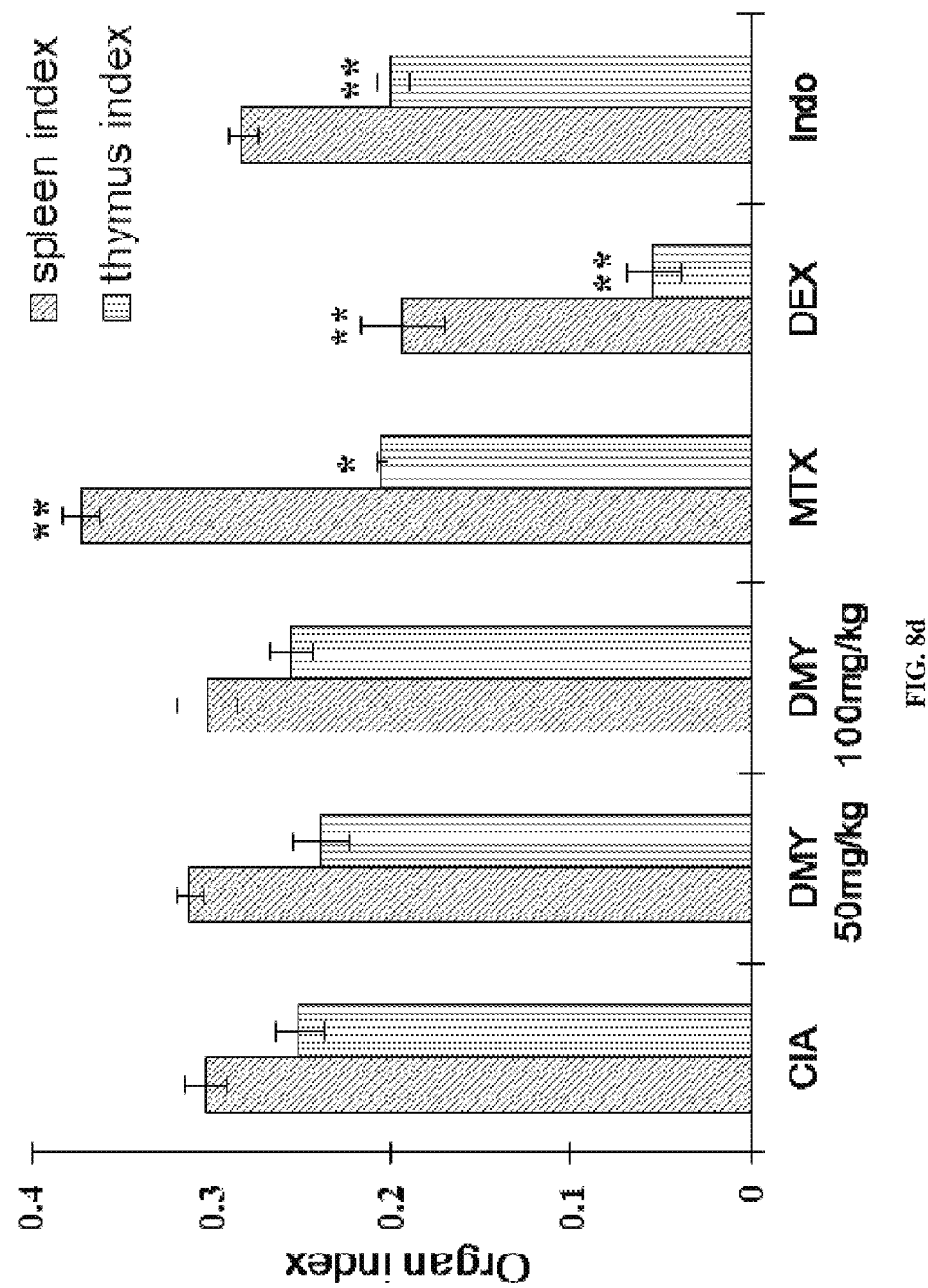
Figure 8E:
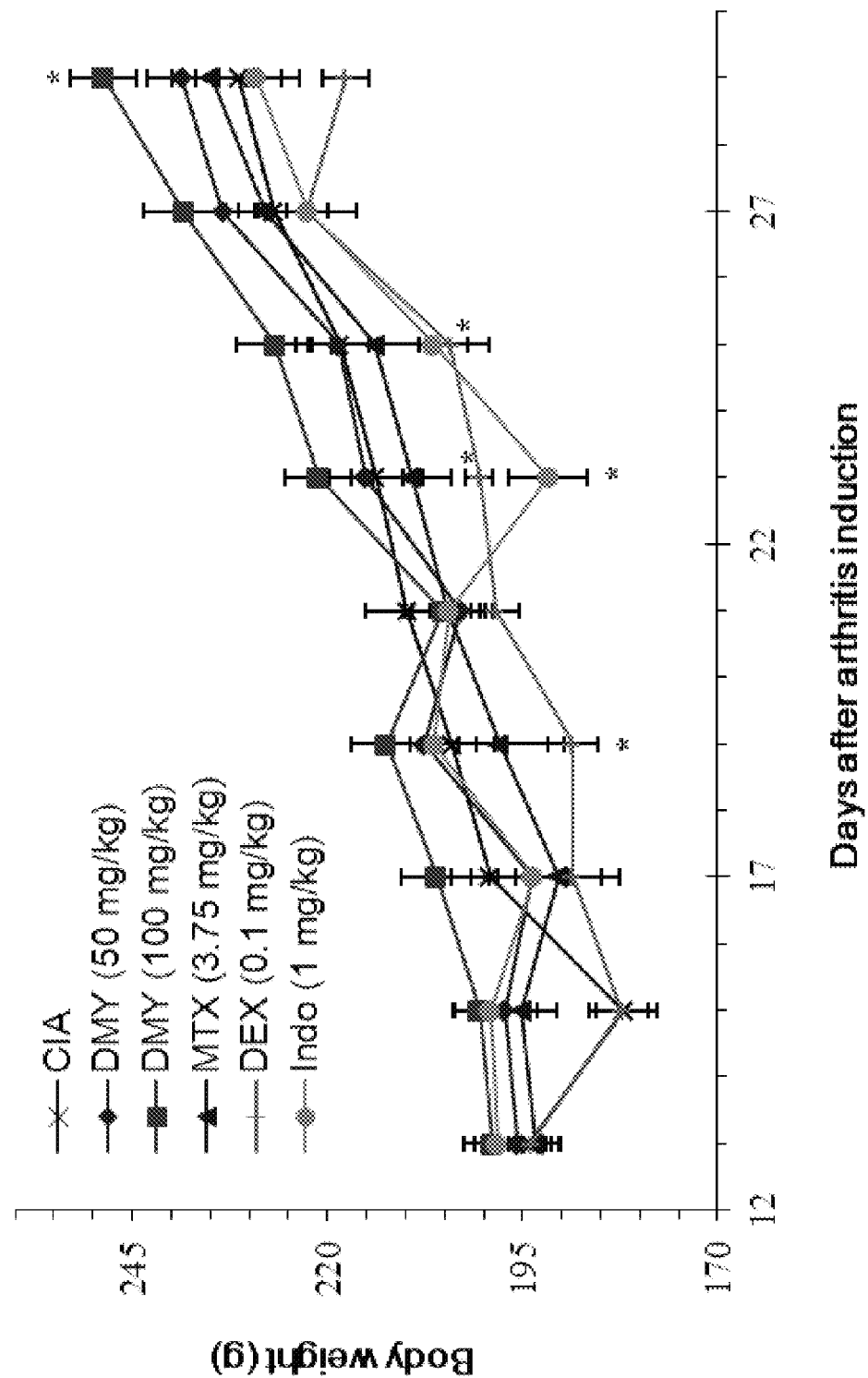

Results:

In contrast to the failure of inflammatory suppression effect of DMY in IKK-$β^{C46A}$ mutant mice, the anti-inflammatory effect of DMY has been further validated in CIA rat models using wild-type animal. In rat CIA model, DMY is demonstrated to significantly decrease hind paw volumes and arthritic scores in rats as compared to vehicle-treated CIA rats (FIGS. 8a & b). Concomitantly, DMY is shown to significantly suppress NF-κB signaling in the knee synovial tissues of CIA rats (FIG. 8c) and has no adverse impairment to the organ indexes of CIA rats (FIG. 8d); it is also able to prevent loss of body weight of CIA rats, compared to the vehicle- and reference reagents-treated animals (FIG. 8e).

Conclusion:

These data demonstrates that DMY exhibits potent anti-inflammatory effect on CIA rat model with wild type IKK-β.

The exemplary embodiments of the present invention are thus fully described. Although the description refers to particular embodiments, it will be clear to one skilled in the art that the present invention may be practiced with variation of these specific details. Hence the present invention should not be construed as limited to the embodiments set forth herein.

CONCLUSION

In summary, the present invention identifies the role of cysteine-46 (Cys-46) on IKK-β kinase in transgenic mice models in modulating inflammatory responses and as a specific drug-binding site to mediate the anti-inflammatory actions of drugs.

In vitro site-directed mutagenesis and in vivo experiments on homozygous IKK-$\beta^{C46A}$ transgenic mice demonstrate that mutated IKK-β kinase has stronger IKK-β kinase activity than wild-type. Severe inflammation and diminished anti-inflammatory potency of dihydromyricetin (DMY), a well-known IKK-β inhibitor which is derived from the medicinal plant *Ampelopsis megalophylla*, are observed in the delayed-type hypersensitivity (DTH) responses in the homozygous IKK-$\beta^{C46A}$ mutant mice, suggesting that Cys-46 is a potent functional site for modulating IKK-β kinase activity and anti-inflammatory responses.

The identification of the specific drug-binding site Cys-46 on IKK-β kinase and establishment of homozygous IKK-$\beta^{C46A}$ transgenic mice should provide new platforms for mechanistic studies of IKK-β-associated inflammation and Cys-46-targeting personalised therapy.

What is claimed is:

1. A homozygous IKK-$\beta^{C46A}$ transgenic, knock-in, C57BL/6J mouse whose genome comprises a transgene encoding a single cysteine-to-alanine mutation at position 46 (C46A) in the endogenous amino acid sequence of SEQ ID NO:2, wherein the transgenic mouse comprises kidney tissues with a stronger in vivo kinase activity of IKK-$\beta$ and ear tissues with an enhanced in vivo inflammatory response to a delay-type hypersensitivity (DTH)-inducing agent relative to an equal amount of the respective tissues from a C57BL/6J wild-type mouse.

2. A method of preparing the homozygous IKK-$\beta^{C46A}$ transgenic, knock-in, C57BL/6J mouse of claim 1, said method comprising:
   (a) transfecting mouse embryonic stem cells by electroporating with a linearized targeting construct with Neo selection gene, wherein said targeting construct is IKK-$\beta^{C46A}$ targeting construct comprising the nucleotide sequence of SEQ ID NO: 1;
   (b) identifying and selecting recombinant embryonic stem cells obtained from step (a) that have undergone correct homologous recombination;
   (c) injecting recombinant embryonic stem cells from step (b) into blastocysts;
   (d) transplanting blastocysts obtained from step (c) into a pseudopregnant mouse to generate chimeric IKK-$\beta^{C46A}$ mice;
   (e) mating chimeric IKK-$\beta^{C46A}$ males obtained from step (d) with C57BL/6J females to produce heterologous IKK-$\beta^{C46A}$ transgenic, knock-in, C57BL/6J mice; and
   (f) mating heterologous IKK-$\beta^{C46A}$ transgenic, knock-in, C57BL/6J mice obtained from step (e) to produce homozygous IKK-$\beta^{C46A}$ transgenic, knock-in, C57BL/6J mouse of claim 1.

3. The method of claim 2, wherein the targeting construct being a template to introduce a single point mutation at the cysteine (C) residue at position 46 in the endogenous amino acid sequence of SEQ ID NO:2 being replaced by alanine (A).

4. The method of claim 2, wherein said recombinant embryonic stem cells are further validated by PCR and gene sequencing using two pairs of forward and reverse primers having SEQ ID NO: 3, SEQ ID NO: 4, SEQ ID NO: 5, and SEQ ID NO: 6.

5. The method of claim 2, wherein said linearized targeting construct contains homology arms of 3.8 kb at 5' arm and 2.5 kb at 3' arm, said homology arms being constructed by PCR using five pairs of forward and reverse primers comprising SEQ ID NOs: 7 to 16.

6. The method of claim 4, wherein the forward and reverse primer pairs having SEQ ID No: 3 and SEQ ID NO: 4 are used to evaluate 5'arm of the genes expressing IKK-$\beta^{C46A}$ mutant for genotyping.

7. The method of claim 4, wherein the forward and reverse primer pairs having SEQ ID NO: 5, and SEQ ID NO: 6 are used to evaluate 3'arm of the genes expressing IKK-$\beta$ mutant for genotyping.

8. A method for determining therapeutic or prophylactic activity of a test compound in delay-type hypersensitivity (DTH) and other inflammatory or cancerous diseases mediated by activation of IKK-$\beta^{C46A}$ mutant protein comprising:
   (a) administering said test compound to the transgenic C57BL/6J mouse of claim 1;
   (b) measuring one or more physiological, morphological, molecular and/or histological parameter(s); and
   (c) comparing the measure in (b) with a measure obtained from a control mouse to observe or analyze any difference between two measures qualitatively and quantitatively in order to determine whether the test compound administered is specific and effective for treating or prophylaxing DTH and other inflammatory or cancerous diseases mediated by activation of IKK-$\beta^{C46A}$ mutant, protein.

9. The method of claim 8, wherein the test compound specifically binds to cysteine 46 residue of the IKK-$\beta$ protein in the epithelial cell in order to inhibit IKK-$\beta$ and NF-$\kappa$B signaling, wherein an activation of said signaling potentially leads to severe inflammatory response or cancerous diseases; otherwise, if the test compound can target IKK-$\beta$ via other binding sites but not on cysteine 46 residue, the activation of IKK-$\beta^{C46A}$ and NF-$\kappa$B signaling pathway can be suppressed.

10. The method of claim 8, wherein the inflammatory or cancerous diseases are selected from a group consisting of arthritis, delay-type hypersensitivity autoimmune disease and various types of cancer with different origin mediated by activation of IKK-$\beta^{C46A}$ mutant protein.

* * * * *